(12) United States Patent
Bhatt et al.

(10) Patent No.: US 7,317,111 B2
(45) Date of Patent: Jan. 8, 2008

(54) GREEN AND ORANGE FLUORESCENT LABELS AND THEIR USES

(75) Inventors: Ram Bhatt, San Diego, CA (US); Michael J. Conrad, Escondido, CA (US); Azzouz Bencheikh, San Diego, CA (US); Yifeng Xiong, San Diego, CA (US)

(73) Assignee: Aries Associates, Inc., San Diego, GA (US)

( * ) Notice: Subject to any disclaimer, the term of this patent is extended or adjusted under 35 U.S.C. 154(b) by 239 days.

(21) Appl. No.: 10/669,584

(22) Filed: Sep. 23, 2003

(65) Prior Publication Data

US 2004/0106806 A1   Jun. 3, 2004

Related U.S. Application Data

(60) Provisional application No. 60/413,025, filed on Sep. 23, 2002.

(51) Int. Cl.
*C07C 309/50* (2006.01)
*C07C 331/24* (2006.01)
*C07D 207/404* (2006.01)
*G01N 21/00* (2006.01)

(52) U.S. Cl. .................. 548/528; 558/17; 562/52; 562/55; 436/172; 436/800

(58) Field of Classification Search ............... 548/528; 558/17; 562/52, 55; 436/172, 800
See application file for complete search history.

(56) References Cited

U.S. PATENT DOCUMENTS

| 4,844,841 | A | * | 7/1989 | Koller et al. ............... 562/55 |
| 5,132,432 | A | | 7/1992 | Haugland et al. |
| 5,514,710 | A | * | 5/1996 | Haugland et al. .......... 514/512 |
| 5,569,366 | A | * | 10/1996 | Chen et al. ................ 204/452 |
| 6,949,632 | B2 | * | 9/2005 | Conrad et al. .............. 536/4.1 |
| 2005/0123935 | A1 | * | 6/2005 | Haugland et al. ............. 435/6 |

FOREIGN PATENT DOCUMENTS

| GB | 1 441 021 | 6/1976 |
| WO | WO90/05916 A1 | 5/1990 |

OTHER PUBLICATIONS

Baustert, J.H. et al. (1988). "Fluorometric Continuous Assay of α-Chymotrypsin Using new Protease Substrates Possessing Long Wavelength Excitation and Emission Maxima." *Analytical Biochemistry*. vol. 171, pp. 393-397.

Chen, F. et al. (1995) "Analysis of mono- and oligosaccharide isomers derivatized with 9-aminopyrene—1,4,6-trisulfonate by capillary electrophoresis with laser-induced Fluorescence." *Analytical Biochemistry*. vol. 230, pp. 273-280.

Chiesa, C. and R.A. O'Neill. (1994) "Capillary zone electrophoresis of oligosaccharides derivatized with various aminonaphthalene sulfonic acids." *Electrophoresis*. vol. 15, pp. 1132-1140.

Csortos, C. et al. (1990) "Interaction of the Catalytic Subunits of Protein Phosphatase-1 and 2-A with Inhibitor-1 and 2: A fluorescent Study with Sulfhydryl specific Pyrene Maleimide." *BBRC*. vol. 169, No. 2, pp. 559-564.

Evangelista, R.A. et al. (1996) "Acid-catalyzed reductive amination of aldoses with 8-amino-pyrene-1,3,6-trisulfonate." *Electrophoresis*. vol. 17, pp. 347-351.

Guttman, A. and T. Pritchett. (1995) "Capillary gel electrophoresis separation of high-mannose type oligosaccharides derivatized by 1-aminopyrene-1,6,8-trisulfonic acid." *Electrophoresis*. vol. 16, pp. 1906-1911.

Jackson, P. (1990) "The use of polyacrylamide-gel electrophoresis for the high resolution separation of reducing saccharides labeled with the fluorophore 8-aminonaphthalene-1,3,6-trisulphonic acid." *Biochem. J.* vol. 270, pp. 705-713.

Karim, A.S. et al. (1995) "Maleimide-mediated protein conjugates of nucleoside triphosphate gamma-S and an internucleotide phosphorothiate diester." *Nucleic Acids Research*. vol. 23, No. 11, pp. 2037-2040.

Weltman, J.K. et al. (1973) "N-(3-pyrene) maleimide: a Long Lifetime Fluorescent Sulfhydryl Reagent." *J. Biol. Chem.* vol. 248, No. 9, pp. 3173-3177.

Koller E. et al. "Longwave Absorbing and Fluorescing Fluorophore for Use in Hydrolast Analysis," *Applied Fluorescence Technology*, Oct. 1989, pp. 15-16, vol. 1, No. 5.

* cited by examiner

*Primary Examiner*—Fiona T. Powers
(74) *Attorney, Agent, or Firm*—Saliwanchik, Lloyd & Saliwanchik

(57) ABSTRACT

The present invention provides novel fluorescent compounds and covalent attachment chemistries which facilitate the use of these compounds as labels for ultrasensitive and quantitative fluorescent detection of low levels of biomolecules. In a preferred embodiment, the fluorescent labels of this invention are novel derivatives of the hydroxy-pyrene trisulphonic and disulphonic acids which may be used in any assay in which radioisotopes, colored dyes or other fluorescent molecules are currently used. Thus, for example, any assay using labeled antibodies, proteins, oligonucleotides or lipids, including fluorescent cell sorting, fluorescence microscopy (including dark-field microscopy), fluorescence polarization assays, ligand, receptor binding assays, receptor activation assays and diagnostic assays can benefit from use of the compounds disclosed herein.

21 Claims, 23 Drawing Sheets

Fig. 1A
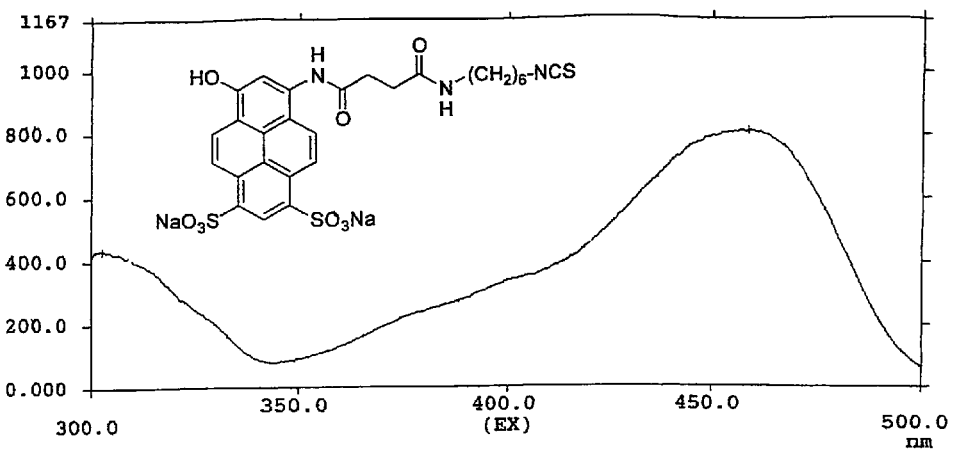
Sample     : ABC-558-59
Comment    : SB Susb.dil pH 9.0
EM : 508.0 nm
Data Mode  : Fluorescence
Scan Speed : 1200 nm/min    Slit (EX/EM) : 2.5 nm / 2.5 nm
PMT Voltage : 700 V   Response : Auto
| No. | WL (nm) | Peak  | No. | WL (nm) | Peak  |
|-----|---------|-------|-----|---------|-------|
| 1   | 302.6   | 435.3 | 2   | 458.6   | 811.9 |
Data                        Peak Data                 12/03/01 02:41 PM
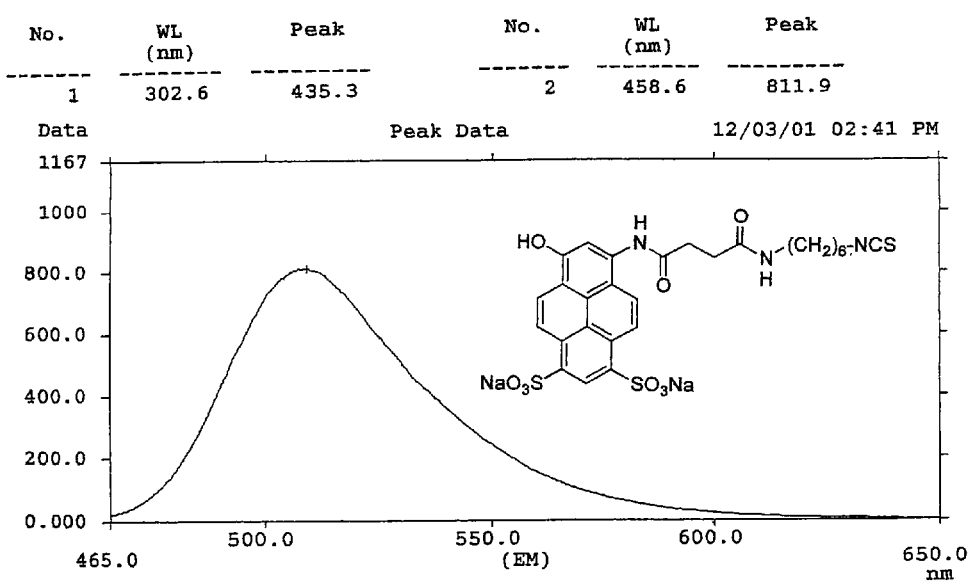
Sample     : ABC-558-59
Comment    : SB Susb.dil pH 9.0
EX : 458.0 nm
Data Mode  : Fluorescence
Scan Speed : 1200 nm/min    Slit (EX/EM) : 2.5 nm / 2.5 nm
PMT Voltage : 700 V   Response : Auto
| No. | WL (nm) | Peak  | No. | WL (nm) | Peak |
|-----|---------|-------|-----|---------|------|
| 1   | 509.0   | 813.4 |     |         |      |

Fig. 1B
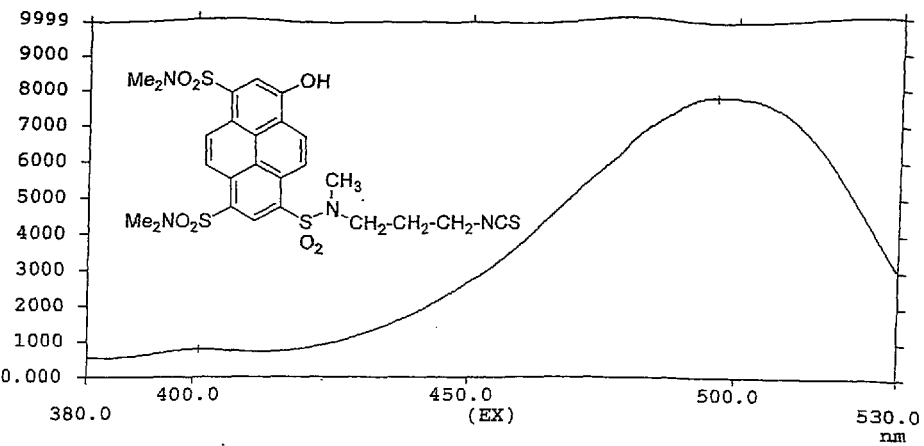
```
Sample   : SBO-R-NCS
Comment  : PBS pH 7.0
EM : 547.0 nm
Data Mode : Fluorescence
Scan Speed : 1200 nm/min   Slit (EX/EM) : 5.0 nm / 5.0 nm
PMT Voltage : 700 V   Response : Auto
```
| No. | WL (nm) | Peak | No. | WL (nm) | Peak |
|---|---|---|---|---|---|
| 1 | 401.0 | 783.5 | 2 | 496.2 | 7881 |
Data      Peak Data      09/10/02 01:02 PM
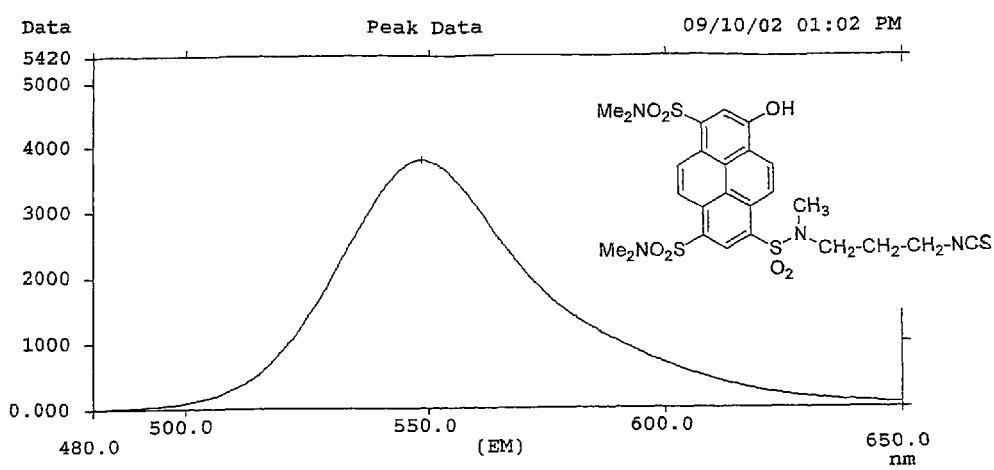
```
Sample   : SBO-R-NCS
Comment  : PBS pH 7.0
EX : 460.0 nm
Data Mode : Fluorescence
Scan Speed : 1200 nm/min   Slit (EX/EM) : 5.0 nm / 5.0 nm
PMT Voltage : 700 V   Response : Auto
```
| No. | WL (nm) | Peak | No. | WL (nm) | Peak |
|---|---|---|---|---|---|
| 1 | 548.4 | 3807 | | | |

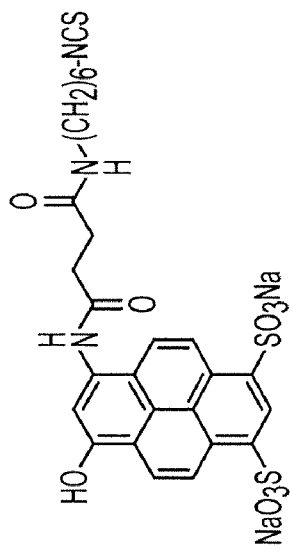
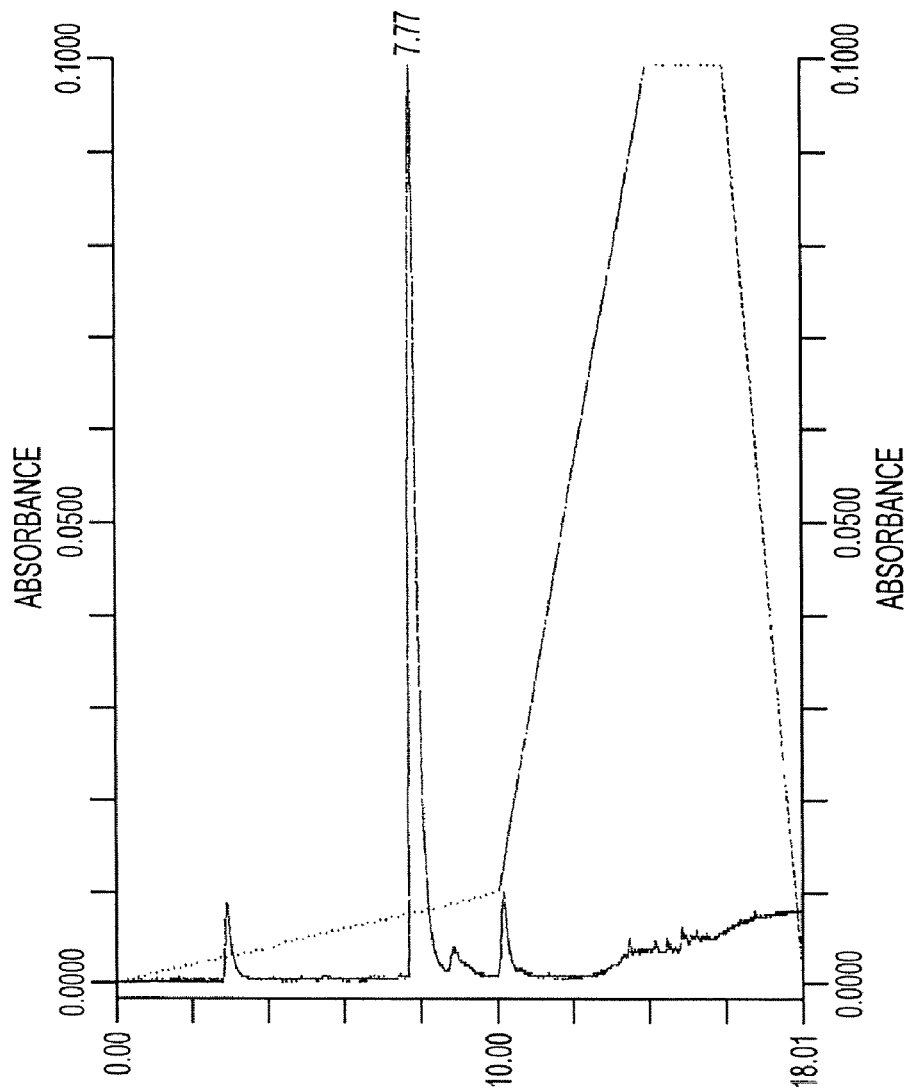
FIG. 6A

GEL SHIFT ASSAY OF SA-SBO 1 2 3 4 5

LANES:
1. SA-SBO ; 1 μg
2. SA-SBO + BIOTIN-IgG; 5 μg
3. SA-SBO ; 10 μg
4. SA-SBO + BIOTIN-IgG; 10 μg
5. BIOTIN-IgG; 5 μg

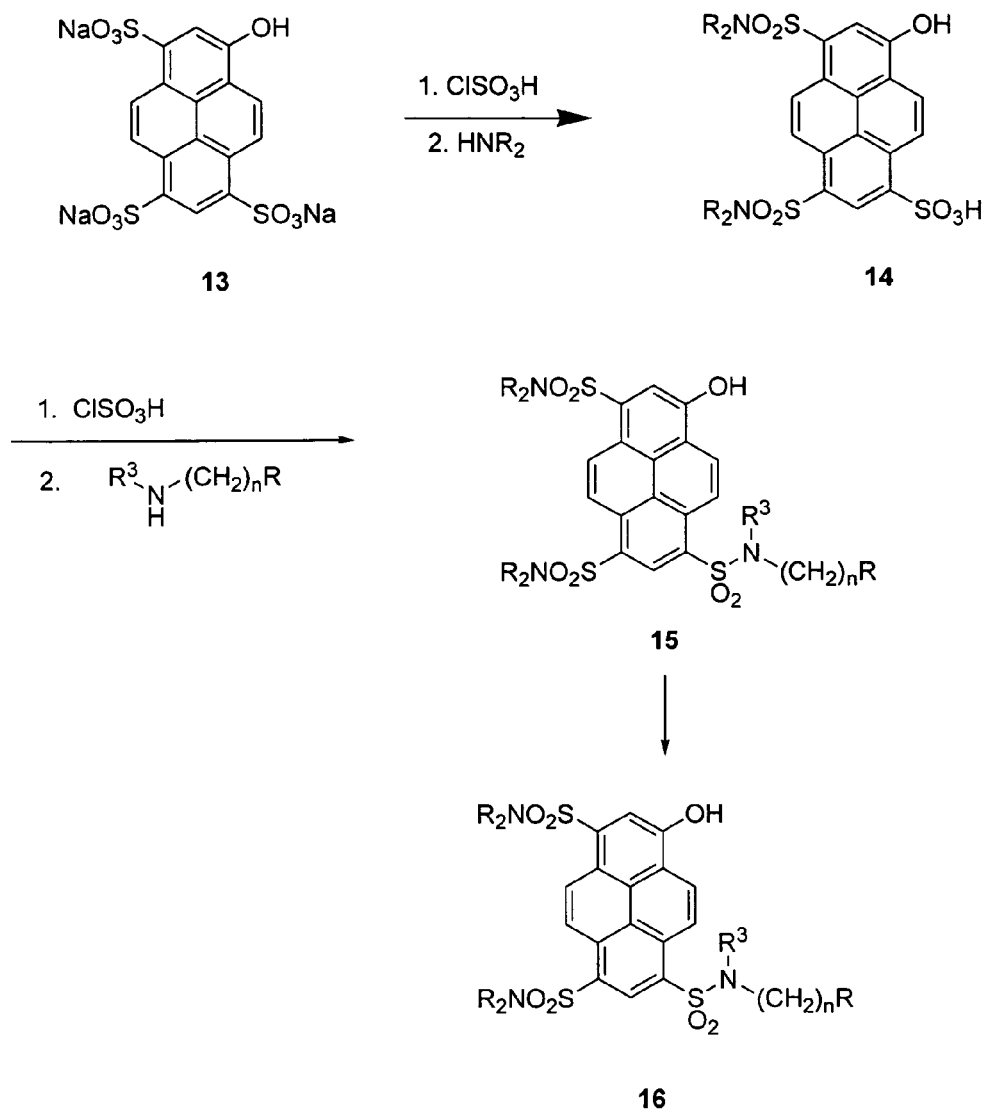
n = 2 - 10
R¹, R² = alkyl groups
R³ = H, alkyl groups,    R⁴ = COOH, NH₂, Biotin
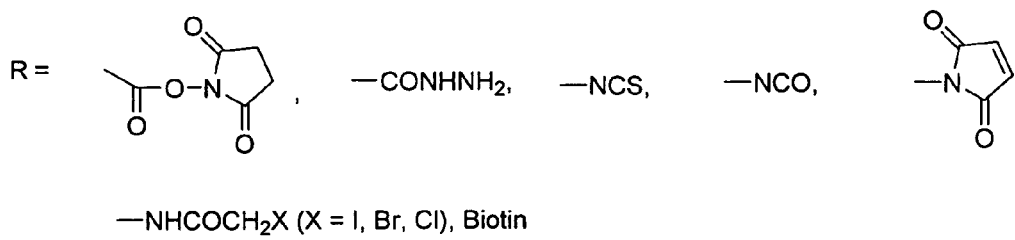
—NHCOCH₂X (X = I, Br, Cl), Biotin
FIG. 19

GREEN AND ORANGE FLUORESCENT LABELS AND THEIR USES

CROSS-REFERENCE TO RELATED APPLICATIONS

This application claims the benefit of U.S. Provisional application No. 60/413,025, filed Sep. 23, 2002.

BACKGROUND OF THE INVENTION

Wider Stoke's shifts, greater water solubility and photostability are key requirements for general acceptance of any new fluorophore. Narrow Stoke's shifts make it difficult to distinguish between actual signal and background signal, and when short wavelength excitation and emission are used, as in dark field fluorescence microscopy, the strong background fluorescence from biological samples can interfere heavily. Since most biological experiments are performed in aqueous solution, fluorescent probes with good water solubility are desirable. Finally, the desired improvements in sensitivity, which drives all attempts to develop new fluorescent labels, requires fluorophores that are photostable and have high quantum yield will be able to achieve high sensitivity.

The potential of pyrene and its derivatives for use in developing improved permanently fluorescent labels for the detection of biological molecules in research and diagnostic applications including fluorescence microscopy, gel electrophoresis, flow cytometry, immunoassays, DNA sequencing, immuno-blotting, nucleic acid probe assays has been under study for more than a century. As a general rule, however, the compounds that were developed proved unsatisfactory because they suffered from narrow Stoke's shifts, photoinstability, low quantum yields, short wave excitation and emissions and/or poor water solubility.

The literature on pyrene and its derivatives regarding uses for fluorescence detection is vast and extends back to the dye chemists of Bayer at the turn of the past century, (cf. Tietze, E., and Bayer, O., *Pyrene Sulfoacids and its Derivatives*, German Reich Patents 343147, 659883, 233934, 664652, and 658780), although the focus of much of this work has been largely on the development of fluorogenic substrates for use in measuring enzymatic activities. Beginning in the 1970s, numerous labs attempted to develop fluorescent labels based on pyrene, with special emphasis on simple derivatives that could be covalently attached though monofunctional substituents on the polyaromatic rings of pyrene itself. Early examples included: (1) synthesis of N-(3-pyrene maleimide) which was subsequently conjugated with proteins and used in early studies of fluorescence polarization (Weltman, J. K, et al, *N-(3-pyrene) maleimide: a Long Lifetime Fluorescent Sulfhydryl Reagent J. Biol. Chem.* 248(9), 3173-3177 (1973)). The same maleimide derivative found continued use through the 1990s in a variety of different biomolecular targets including: (i) phosphatases (Csortos, C., et al, *Interaction of the Catalytic Subunits of Protein Phosphatase-1 and 2-A with Inhibitor-1 and 2: A fluorescent Study with Sulfhydryl specific Pyrene Maleimide* BBRC 169 (2), 559-564 (1990)), and, (ii) of the interaction of the fluorophore with nucleoside analogs (Karim, A. S., et al, *Maleimide-mediated protein conjugates of nucleoside triphosphate gamma-S and an internucleotide phosphorothiate diester, Nucleic Acids Research*, 23 (11), 2037-2040 (1995)). These compounds suffered from two major limitations, however: (i) poor water solubility of the core pyrene molecule, and, (ii) fluorescence quenching in aqueous buffers.

In an effort to overcome the solubility limitations, numerous labs began to experiment with 8-aminonaphthalene-1,3,6-trisulphonic ("ANTS") acid derivatives of pyrene, particularly as a label for use in identifying glycoconjugates in electrophoretic gels (cf., (i) Jackson, P., *The use of polyacrylamide-gel electrophoresis for the high resolution separation of reducing saccharides labelled with the fluorophore 8-aminonaphtalene-1,3,6-trisulphonic acid, Biochem. J.* 270, 705-713 (1990), and, (ii) Chiesa, C., and O'Neill, R. A., *Capillary zone electrophoresis of oligosaccharides derivatized with various aminonaphthalene sulfonic acids, Electrophoresis* 15, 1132-1140 (1994), (iii) Evangelista, R. A., Guttman, A., and Chen, Fu-Tai, *Acid-catalyzed reductive amination of aldoses with 8-amino-pyrene-1,3,6-trisulfonate, Electrophoresis* 17, 347-351 (1996), Guttman, A. and Pritchett, T., *Capillary gel electrophoresis separation of high-mannose type oligosaccharides derivatized by 1-aminopyrene-1,6,8-trisulfonic acid, Electrophoresis* 16, 1906-1911 (1995), and, (iv) Evangelista, R. and Chen, Fu-tai, *Analysis of mono-and oligosaccharide isomers derivatized with 9-aminopyrene-1,4,6-trisulfonate by capillary electrophoresis with laser-induced Fluorescence, Analytical Biochemistry* 230, 273-280 (1995)). A related derivative, 5-(2-(iodoacetyl)-amino) ethyl) aminonaphtalene-1-sulfonic acid ("1,5-I-AEDANS") was used in functionalizing nucleosides (cf., Agrawal, S, and Zamecnik, P. C. *Site specific functionalization of oligonucleotides for attaching two different reporter groups, Nucleic Acids Research* 18 (18), 5419-5423 (1996)). In another application of pyrene to nucleoside labeling, Crisp and Gore reported (Crisp, G. T. and Gore, J., *Palladium-catalysed Attachment of Labels with Acetylenic Linker Arms to Biological Molecules, Tetrahedron* 53 (4), 1523-1544 (1997)) coupling of the core pyrene fluorophore through propoargylglycine spacers to the 8-alynyl derivatives of adenosine and guanosine, however, this work was never applied to labeling of any biomolecule owing to the quenching limitations noted earlier for the core pyrene fluorophore in aqueous solvents.

Quite different types of applications were developed by Nomura et al and, separately, Wolfbeis et al. In the first, 8-hydroxy-1,3,6-pyrenetrisulfonate has been conjugated to lipids to make the fluorophore more hydrophobic and the conjugates used to measure energy transfer in surfactant vesicles (Nomura, T., et al, *Aspects of Artificial Photosynthesis. Energy Transfer in Cationic Surfactant Vesicles, JACS* 102 (5), 1484-1488 (1980)). Koller and Wolfbeis extended the much earlier work of Tietze et al, throughout the 1980s, but focused largely on the fluorogenic applications and did not attempt to develop or apply any labels of the pyrene sulfonic acids (cf., (i) Koller, E. and Wolfbeis, O., *Continuous Kinetic Assay of Arylsulfatases with New Chromagenic and Fluorogenic Substrates, Analytica Chimica Acta* 170, 73-80 (1985), and, (ii) Baustert, J. H., et al, *Fluorometric Continuous Assay of α-Chymotrypsin Using new Protease Substrates Possessing Long Wavelength Excitation and Emission Maxima, Analytical Biochemistry* 171, 393-397 (1988)). The sole exceptions to this focus on fluorogenic substrates in Koller's work were reported in 1989 in an article describing the lipophilic monoesters and diesters of monohydroxy pyrene trisulfonate and dihydroxypyrene disulfonate, respectively (Koller, E., *Pyrene Sulfonates: An interesting class of fluorescent probes, Applied Fluorescence Technology* 1, 13-14 (1989)).

In the early 1990s, Haugland and his colleagues (Whitaker, et al, *Cascade Blue Derivatives: Water Soluble, Reactive Blue emission Dyes Evaluated as Fluorescent Labels and Tracers, Biochemistry* 198, 119-130 (1991)) attempted to develop a panel of biological labels based upon water soluble derivatives of pyreneloxytrisulfonic acid which they designated "Cascade Blue" in recognition of the emission wavelengths of the

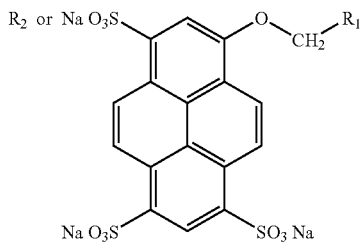

where $R_1$ was chosen from the following panel of 20 esterified spacers comprising from 2 to approximately 15 carbons, with some spacers including dextran, t-BOC protecting groups, nitrogen, fluorine and oxygen as additional substituents:

| | |
|---|---|
| 1 | $COCH_3$ |
| 2 | $CO_2H$ |
| 3 | $CONH(CH_2)_2NH_2$ |
| 4 | $CONH(CH_2)_6NH_2$ |
| 5 | $CONH\text{-}DEXTRAN\text{-}NH_2$ |
| 6 | $CONH(CH_2)_2NHCOCl$ |
| 7 | $CONH(CH_2)_6NHCOCH_2I$ |
| 8 | $CO_2\text{-}SUCC$ |
| 9 | $CON_3$ |
| 10 | $CONH(CH_2)_2OH$ |
| 11 | $CONHNH_2$ |
| 12 | $CONHNH_2$ |
| 13 | $CONHNH_2$ |
| 14 | $CONH(CH_2)_2NHCOCH(CH_2)_3N\text{-}t\text{-}BOC$ |
| 15 | $CONH(CH_2)_6NHCOCH(CH_2)_3N\text{-}t\text{-}BOC$ |
| 16 | $CONH(CH_2)_6CN$ |
| 17 | $CONH(CH_2)_2NHCOCH(CH_2)_3NH\bullet(CF_3CO_2H)$ |
| 18 | $CONH(CH_2)_6NHCOCH(CH_2)_3NH\bullet(CF_3CO_2H)$ |
| 19 | $CONH(CH_2)_6NHCOCH{:}CH_2$ |
| 20 | $CONH(CH_2)_6NHCO(C_6H_6)N_3$ |
| 21 | $CO_2CH_3$ where $R_2 = OCH_2CO_2CH_3$ |
| 22 | $CO_2CH_3$ where $R_2 = {-}OH$ |
| 23 | $CO_2H$ where $R_2 = OCH_2CO_2H$ |
| 24 | $CO_2H$ where $R_2 = {-}OH$ |

The general method of synthesis was condensation of an alkylating reagent such as an appropriately substituted alkyl halide, in the presence of a base, with a substituted or unsubstituted pyrene trisulfonic acid having a hydroxyl in the 1, 3, 6, or 8 position to give an alkoxy intermediate which was then hydrolyzed or reacted directly with hydrazine or aliphatic amines to give derivatives having the desired spacer and terminal functional group. Derivatives with terminal amines were further reacted with activated carboxylic acid derivatives, such as the succinimidyl esters of compounds possessing the desired additional reactive functional groups. In general, these Cascade Blue labels displayed 50 nanometer bandwidths, Stoke's Shifts valued between 20 and 30 nm, blue emission and relatively low molecular brightness, although quantum efficiencies were higher than with other blue emitting dyes (cf. Chemically reactive pyrenyloxy sulfonic acid dyes, U.S. Pat. No. 5,132,432 issued Jul. 21, 1992).

BRIEF SUMMARY

The present invention provides novel fluorescent compounds and covalent attachment chemistries that facilitate the use of these compounds as labels for ultrasensitive and quantitative fluorescent detection of low levels of biomolecules.

In a preferred embodiment, the fluorescent labels of the subject invention are novel derivatives of the hydroxypyrene trisulphonic and disulphonic acids. These labels may be used as described herein in any assay in which radioisotopes, colored dyes or other fluorescent molecules are currently used. Thus, for example, any assay using labeled antibodies, proteins, oligonucleotides or lipids, including fluorescent cell sorting, fluorescence microscopy (including dark-field microscopy), fluorescence polarization assays, ligand, receptor binding assays, receptor activation assays and diagnostic assays can benefit from use of the compounds disclosed herein.

In a preferred embodiment, novel fluorescent, hydroxyamino-pyrene sulphonates, hydroxyamino-halopyrene sulphonates, and their derivatives are provided by the subject invention.

The subject invention further provides methods for the derivatization and purification, at both small and large scale levels of preparation.

Additionally, the subject invention provides methods for the covalent conjugation of these novel fluorophores to useful proteins, peptides, nucleosides and nucleotides, oligonucleotides and lipids, and their use as detectable labels for biological applications.

Applications of these new labels for the ultrasensitive detection and measurement of proteins, peptides, oligonucleotides, or lipids using homofunctional and heterobifunctional linkers combined with fluorescence polarization, fluorescence detection and fluorogenic detection are also presented.

Using the materials and methods of the subject invention, detection of molecular targets and interactions in living cells, the components of cell lysates and fixed cells is not limited to the nuclear compartment but can be accomplished in the cytoplasm, the cell surface, organelles, between any of those entities, in components extracted and isolated from cells, and in recombinant, synthetic or enzymatically replicated copies of any components thereof.

In one embodiment, the subject invention utilizes novel compositions comprising synthetic peptides that replicate biologically active proteins or peptides.

Homogeneous applications enabled by these new fluorescent labels and detection chemistries include in vitro fluorescence polarization assays for the detection of enzyme activities, DNA-protein, DNA-RNA and Protein-Protein interactions, and novel methods for simultaneous multiplex screening thereof.

In another embodiment, unique liquid and solid phase heterogeneous applications are made possible using these new chemistries. This facilitates the creation and use of ultra-sensitive in vitro fluorescent assays of general or specific uses in fluorescence microscopy, microarrays, microtiter plate assays, fluorescence-based cell sorting, reverse transcription and reverse transcription/PCR, and gel electrophoresis.

In yet another embodiment, the subject invention provides novel compositions comprising fusion proteins for use in the detection of interactions between fusion proteins and molecules of interest involving two or more inactive, but weakly-complementing enzyme components including but not limited to such enzymes as β-galactosidase, alkaline phosphatase and β-lactamase.

These new fluorophores, detection chemistries, methods and assays facilitate simultaneous multi-plexing detection and profiling of biological and clinical targets. Accordingly, among the uses of the invention are the study of protein-protein interactions, functional genomics, post-translational modification and processing, signal transduction, agonist and antagonist screening, toxicogenomics and new drug discovery.

BRIEF DESCRIPTION OF SEQUENCES

SEQ ID NO: 1 shows a chemically synthesized PCT primer.

SEQ ID NO: 2 shows a chemically synthesized oligonucleotide obtained by treating MMT-NH-oligonucleotide with 80% acetic acid.

BRIEF DESCRIPTION OF THE DRAWINGS

FIGS. 1A and 1B show the excitation and emission spectra of the StarBright Green (SBG) 6, and StarBright Orange (SBO) compound 16, respectively, of this invention

FIGS. 6A and 6B show the elution profiles of the purification of SBG (compound 6) and SBO (compound 16), using reversed phase ($C_{18}$) HPLC.

FIG. 19 shows a first synthetic pathway for the synthesis of StarBright Orange (SBO) labels.

DETAILED DISCLOSURE

Figure 2:
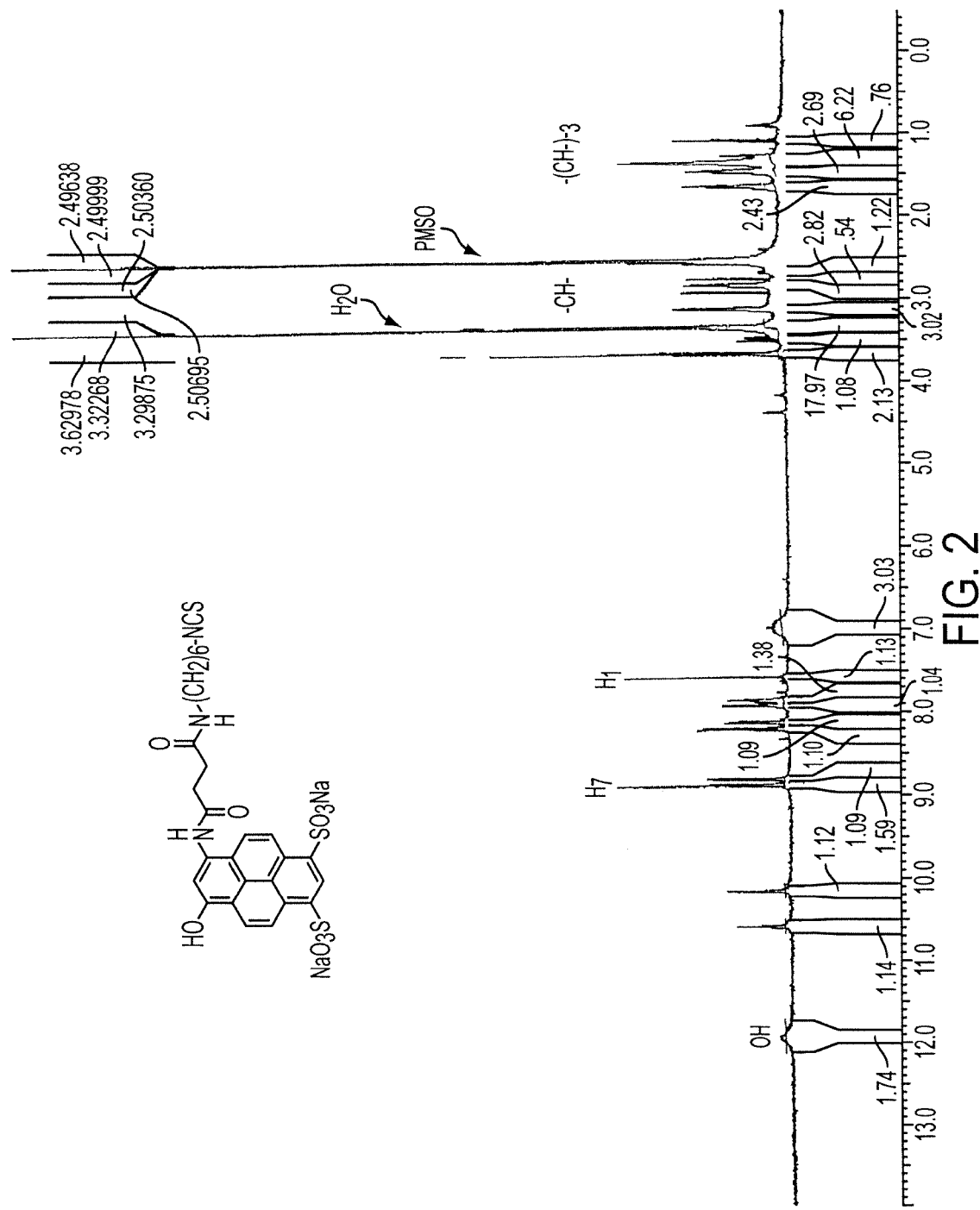
FIG. 2 is a proton NMR spectrum of one embodiment of SBG, compound 6, where $R^1$=NCS (scheme 1), of the StarBright Green label of this invention.
Figure 3:
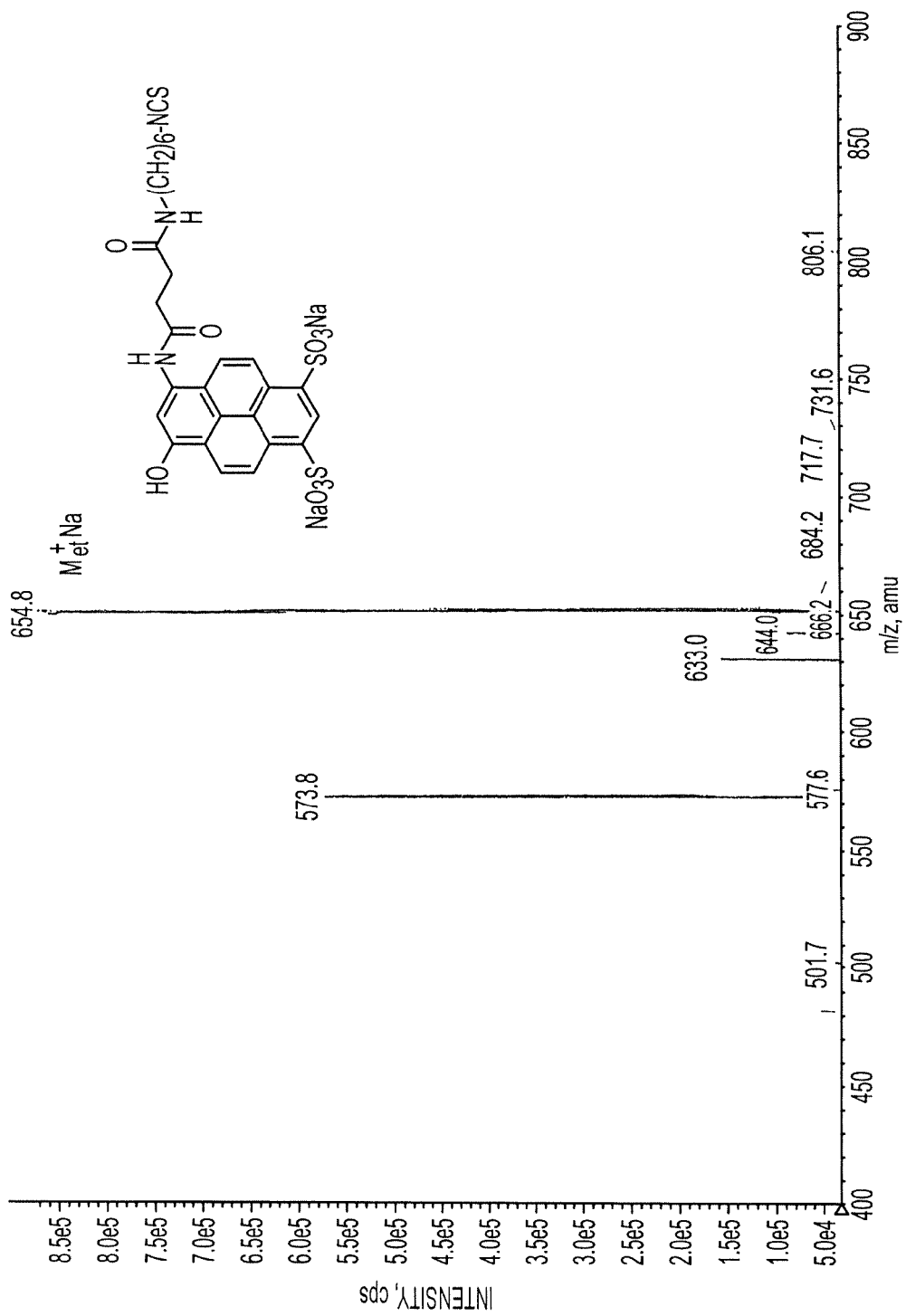
FIG. 3 is a Mass Spectrum of one embodiment, 6, of the StarBright Green label of this invention.
Figure 4:
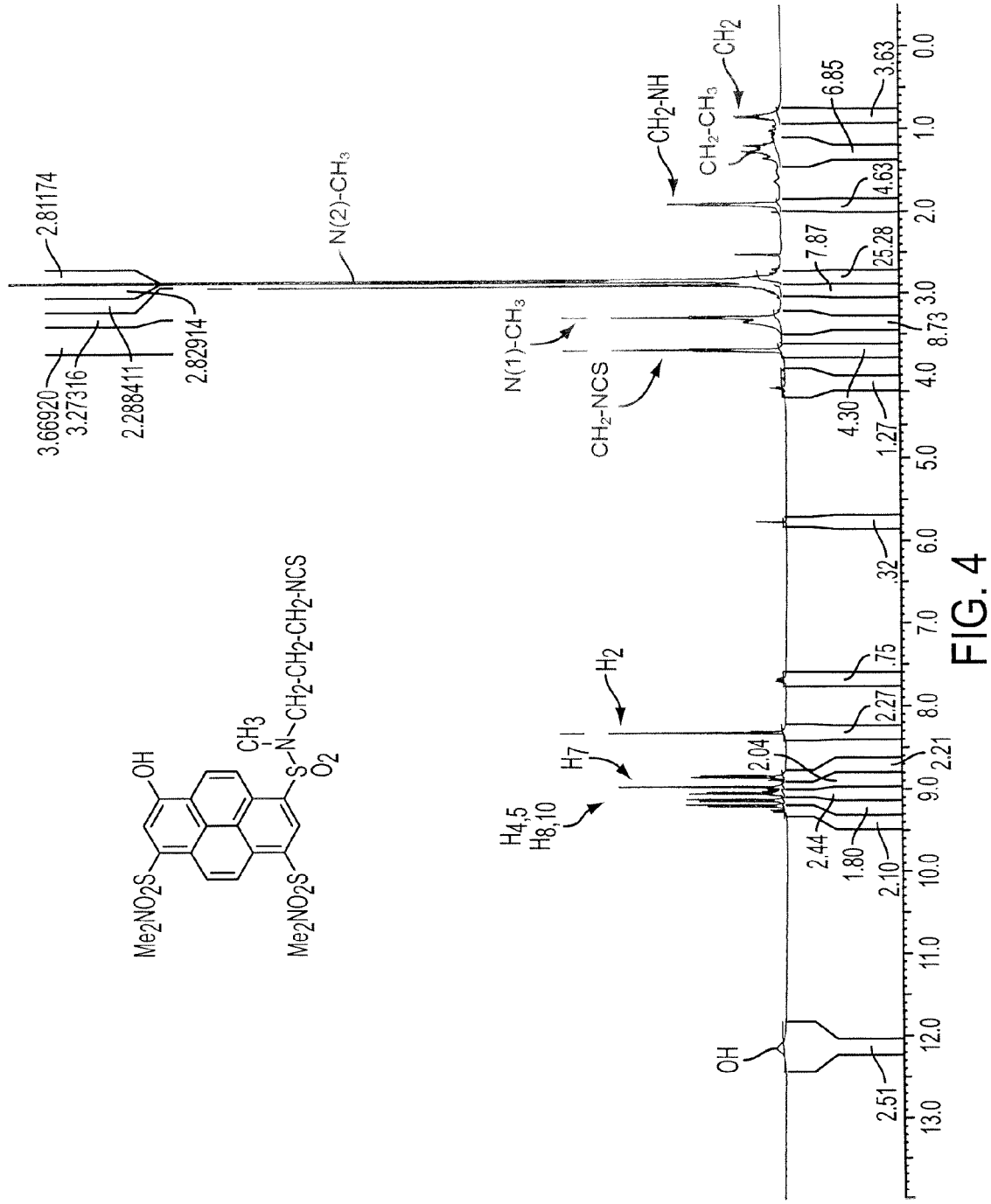
FIG. 4 is a proton NMR spectrum of one embodiment of SBO, compound 16, where $R_2$=$R^3$=Me, n=3, R=NCS (scheme 4) of the StarBright Orange label of this invention.
Figure 5:
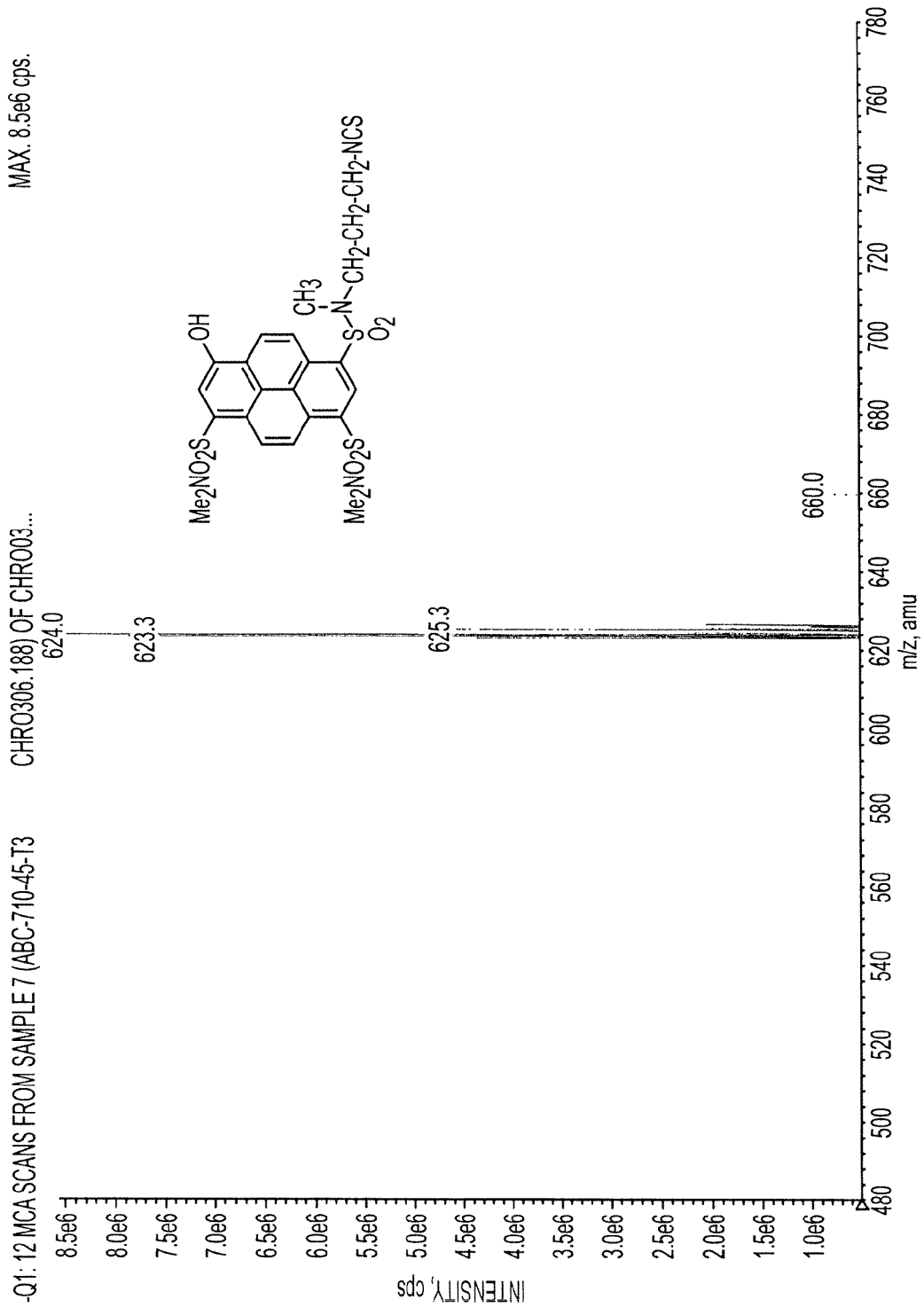
FIG. 5 is a mass spectrum of one embodiment of SBO, compound 16, where $R_2$=$R^3$=Me, n=3, R=NCS (scheme4) of the StarBright Orange label of this invention.

The present invention provides novel fluorescent compounds and covalent attachment chemistries that facilitate the use of these compounds as labels for ultrasensitive and quantitative fluorescent detection of low levels of biomolecules.

In a preferred embodiment, the fluorescent labels of the subject invention are novel derivatives of the hydroxypyrene trisulphonic and disulphonic acids. These labels may be used as described herein in any assay in which radioisotopes, colored dyes or other fluorescent molecules are currently used. Thus, for example, any assay using labeled antibodies, proteins, oligonucleotides or lipids, including fluorescent cell sorting, fluorescence microscopy (including dark-field microscopy), fluorescence polarization assays, ligand, receptor binding assays, receptor activation assays and diagnostic assays can benefit from use of the compounds disclosed herein.

In a preferred embodiment, novel fluorescent, hydroxyamino-pyrene sulphonates, hydroxyamino-halopyrene sulphonates, and their derivatives are provided by the subject invention.

The subject invention further provides methods for the derivatization and purification, at both small and large scale levels of preparation.

Additionally, the subject invention provides methods for the covalent conjugation of these novel fluorophores to useful proteins, peptides, nucleosides and nucleotides, oligonucleotides and lipids, and their use as detectable labels for biological applications.

Applications of these new labels for the ultrasensitive detection and measurement of proteins, peptides, oligonucleotides, or lipids using homofunctional and heterobifunctional linkers combined with fluorescence polarization, fluorescence detection and fluorogenic detection are also presented.

Using the materials and methods of the subject invention, detection of molecular targets and interactions in living cells, the components of cell lysates and fixed cells is not limited to the nuclear compartment but can be accomplished in the cytoplasm, the cell surface, organelles, between any of those entities, in components extracted and isolated from cells, and in recombinant, synthetic or enzymatically replicated copies of any components thereof.

In one embodiment, the subject invention utilizes novel compositions comprising synthetic peptides that replicate biologically active proteins or peptides.

Homogeneous applications enabled by these new fluorescent labels and detection chemistries include in vitro fluorescence polarization assays for the detection of enzyme activities, DNA-protein, DNA-RNA and Protein-Protein interactions, and novel methods for simultaneous multiplex screening thereof.

In another embodiment, unique liquid and solid phase heterogeneous applications are made possible using these new chemistries. This facilitates the creation and use of ultra-sensitive in vitro fluorescent assays of general or specific uses in fluorescence microscopy, microarrays, microtiter plate assays, fluorescence-based cell sorting, reverse transcription and reverse transcription/PCR, and gel electrophoresis.

In yet another embodiment, the subject invention provides novel compositions comprising fusion proteins for use in the detection of interactions between fusion proteins and molecules of interest involving two or more inactive, but weakly-complementing enzyme components including but not limited to such enzymes as β-galactosidase, alkaline phosphatase and β-lactamase.

These new fluorophores, detection chemistries, methods and assays facilitate simultaneous multi-plexing detection and profiling of biological and clinical targets. Accordingly, among the uses of the invention are the study of protein-protein interactions, functional genomics, post-translational modification and processing, signal transduction, agonist and antagonist screening, toxicogenomics and new drug discovery.

In a preferred embodiment, the subject invention provides water soluble, fluorescent compounds that have excitation maxima in both the ultraviolet and visible regions of the electromagnetic spectrum, and a relatively narrow fluorescence emission with a single emission maximum in the useful regions of the visible spectrum when excited by light at either excitation maximum. Additional unique properties that make these structures of value in aqueous fluorescent detection of biological molecules include, but are not limited to:

high quantum yields of excitation and emission,
high photostabilities when exposed to either ultraviolet or visible light,
large Stoke's shifts;
resistance to photoquenching in high local concentrations,
excellent water solubilities, and,
useful structural sites for derivatization and conjugation.

In a preferred embodiment, these fluorescent probes utilize hydroxyamino pyrene sulphonate as the parent structure.

Definitions and Terms

Biochemical Assays are in vitro assays that, for the purposes of the present invention are conducted using neat solutions of enzymes and are not performed in: i) intact biological cells, ii) biological fluids such as cell lysates, serum, or iii) the presence of biological materials other than those that are directly needed as reagents or components of the assay Binding Moieties—refers to at least two molecular species which interact with each other to form a stable complex, including but not limited to (i) antibodies and their epitopes, (ii) complementary DNA sequences, and, (iii) inactive but complementary subunits of an enzyme which, when combined form an active enzyme.

Cell-Based Assays are in vivo or in vitro assays that, for the purposes of the present invention, can be used to detect, for example, the activity of one or more kinase or phosphatase enzymes in intact biological cells, or, alternatively, in biological fluids, including cell lysates or serum.

Fluorescence Detection Methods is a rubric for three different analytical methods that are described in this patent:
(i) Molecular Intensity is the molecular brightness or intensity of the fluorescence emission from a sample over a defined period of time and is typically measured by either signal averaging methods or photon counting methods, both of which are known to one skilled in the art of fluorescence detection;
(ii) Fluorescence Polarization is the emission of light in a defined plane relative to the plane of the polarized light used to excite fluorophores in a sample; and
(iii) Fluorogenesis is the enzymatic, chemical or physical conversion of a molecule from a state in which it is either not fluorescent or is not fluorescent at prescribed emission wavelengths into a different state in which it is fluorescent at the prescribed emission wavelengths.

Heterobifunctional Linkers (cf., Schemes 1 through 6)—any of a class of small molecules that have two different reactive groups that covalently conjugate or electrostatically bind to distinct complementary groups but which do not measurably cross-react with each other or with the complementary group of the other. Specifically, for the purposes of the present invention, one of the functional groups reacts covalently and specifically with reactive groups such as amines, sulfhydryls, carboxyls or with other bioconjugation groups such as avidin.

Monofunctional Linkers (cf., Schemes 1 through 6)—any of a class of small molecules that have a single reactive group that covalently conjugates or electrostatically binds to a distinct complementary group. Specifically, for the purposes of the present invention, the functional group reacts covalently and specifically with the functional groups reacts covalently and specifically with reactive groups such as amines, sulfhydryls, and carboxyls or with other bioconjugation groups such as avidin.

Liquid Phase/Solid Phase—Liquid phase reactions are performed entirely in solvent with all reagents and final products free to rotate in the solutions in which the reactions are performed. In solid phase reactions at least one reagent critical to a reaction is immobilized on an otherwise unreactive solid surface such as the sides and bottom of a microwell or the surface of a bead.

Multi-plexing—the ability of an assay or measurement to detect and quantify several targets at the same time in the same assay or device.

Oligonucleotide and, by inclusion nucleic acids, nucleosides and nucleotides—polymers and monomers of nucleosides and nucleotides of any length. The polymer may be linear, circular or branched, it may comprise modified nucleotides such as those used in protein nucleic acids, and it may be interrupted by non-nucleosides. Also included in the definition are in vitro transcripts and reporter genes, as well as the vectors used for transfection and for the formation of fusion proteins.

Protein, polypeptide and peptide are used interchangeably herein to refer to polymers of amino acids of any length.

The polymer may be linear or branched, it may comprise modified amino acids, and it may be interrupted by non-amino acids, It may also be modified naturally or by intervention, for example disulfide bond formation, glycosylation, myristoylation, acetylation, alkylation, phosphorylation or de-phosphorylation, biotinylation or avidinylation, or through conjugation using any of the conjugation chemistries taught herein or which are known to one knowledgeable in the art. Also included in the definition are fusion proteins, polyclonal antibodies and monoclonal antibodies and polypeptides containing one or more amino acid analogs as well as other modification known in the art.

Linker—a fluorophore used to create a detectable reporter unit is generally covalently conjugated either directly or through an otherwise inert but water soluble spacer, to a biding moiety that confers some type of target specificity for a second biding unit which is generally the target of interest. The reactive components that evoke the covalent attachment of the two is referred to as a linker. For example, when the reporter unit is a StarBright Green labeled IgG molecule, the linker may be a succinimidyl ester that covalently attaches to the —NH2 groups of the antibody. Similarly, the same label may be covalently attached to the 5'-amino group of a chemically synthesized oligonucleotide to create a StarBright Green labeled primer for use in RT/PCR.

Signal Transduction—Signal transduction generally refers to the transfer of information from the exterior of a cell membrane into the cytoplasm, and, in some cases, into the nucleus, wherein the information evokes some cellular response.

Signal Transduction Receptors and Pathways—may involve ion transport and/or combinations of kinase and phosphatase activities to convey information from the cell membrane to its nucleus. Such combinations are generally referred to as cascades and involve kinase and phosphatase activities of three general classes:
1. Receptors that penetrate the plasma or intracellular membranes and have intrinsic enzymatic activities: Receptors that have intrinsic enzymatic activities include, but are not limited to those with: i) tyrosine protein kinase and phosphatase activities, ii) serine/threonine protein kinase and phosphatase activities, and, iii) several activators of phosphatidyl inositol. Receptors with intrinsic tyrosine kinase activity are capable of autophosphorylation as well as phosphorylation of other substrates. Additionally, several families of receptors lack intrinsic enzyme activity, yet are coupled to intracellular tyrosine kinases by direct protein-protein interactions.
2. Receptors that are coupled, inside the cell, to GTP-binding and hydrolyzing proteins (termed G-protein coupled receptors or GPCRs). Receptors of the class that interact with G-proteins all have a structure that is characterized by 7 transmembrane spanning domains. These receptors are termed serpentine receptors. Examples of this class are the adrenergic receptors, odorant receptors, and certain hormone receptors (e.g. angiotensin, vasopressin and bradykinin).
3. Receptors that are found intracellularly and upon ligand binding migrate to the nucleus where the ligand-receptor complex directly affects gene transcription. In general, the polynucleotide kinases and phosphatases are of this type of receptor.

Reporter and Reporter Subunit—As used herein, the terms reporter and reporter subunit refers to any complex of two or more subunits which are capable of associating with one or more biological targets to generate a detectable signal that may be used to detect and quantitate the presence or absence of the target.

Spacer—a molecular connector used to chemically attach two molecular structures that were originally distinct. Specifically, a fluorescent label may be attached through a spacer that bears a homofunctional linker such as a succinimidyl ester at its distal end.

Target Amplification Primers and by example, RT/PCR— short oligonucleotides that, owing to their specific nucleotide sequences, can hybridize to an oligonucleotide (the "template") containing one complementary sequence and, under standard conditions of thermal cycling in the presence of DNA polymerase and nucleoside triphosphates, be used to replicate multiple full length copies of both the template and its complementary oligonucleotide.

The present invention provides a new class of highly fluorescent water-soluble compounds. In a preferred embodiment, these compounds are derivatives of the amino-hydroxy-pyrene-trisulfonic and amino-hydroxy-pyrene-disulfonic acids which are useful as fluorescent labels for detecting biological molecules.

Unlike previously reported pyrene-trisulfonic acid and pyrene-disulfonic acid fluorogenic enzyme substrates, which are not fluorescent until converted into fluorophores by catalytic enzyme action and which are never covalently attached to biological targets for use, these new compounds are permanently fluorescent labels which must be covalently attached to biological targets for use. Similarly, unlike the previously reported pyrene-trisulfonic acid and pyrene-disulfonic acid fluorescent labels, such as the Cascade Blue esters, the present invention takes advantage of the discovery that the monohydroxy and dihydroxy pyrene sulfonates undergo a pH dependent tautomeric shift in emission from a low level, blue fluorescence to an extremely bright, green or orange fluorescence under neutral to basic pH conditions.

In accordance with the subject invention, the pH at which the anion is formed can be shifted to a range useable for biological work if the core aromatic ring structure of hydroxypyrene sulfonate is derivatized to (i) preserve the dissociable proton on the substituent hydroxyl group, and, (ii) elsewhere on the aromatic ring structure, electron withdrawing or donating groups are covalently attached as part of the spacers used to attach monofunctional linkers used to convert the dye to a label.

Preferred compounds of the present invention are polyaromatic, polar molecules that retain the high solubilities of the parent hydroxy-pyrene trisulfonates and disulphonates in aqueous media, but which are excited at ultraviolet and visible wavelengths, have molecular weights ranging from approximately 400 to 700 daltons and display Stokes' shifts greater than 60 nm at visible emission wavelengths.

These new labels are intensely fluorescent amino-hydroxy-pyrene tri- and di-sulfonates and their halo-hydroxy-pyrene sulfonate derivatives that are highly stable to photobleaching which can be of great value in assays requiring stable fluorescent labels. Because of their large Stoke's shifts, typically in excess of 60 nm, the labels do not readily photoquench; their large Stoke's shifts and large quantum yields of emission enable applications in assays requiring great sensitivity and broad dynamic range.

It is a further embodiment of the present invention that the structures of these fluorophores incorporate molecular spacers which bear homofunctional linkers at their distal ends and through which the fluorophore can be covalently attached as a fluorescent label to another, non-fluorescent molecule such as a protein, oligonucleotide, lipid, small molecule ligand or a peptide.

In a preferred embodiment, the substrates of the subject invention have the general formula represented by the structures (I) or (II):

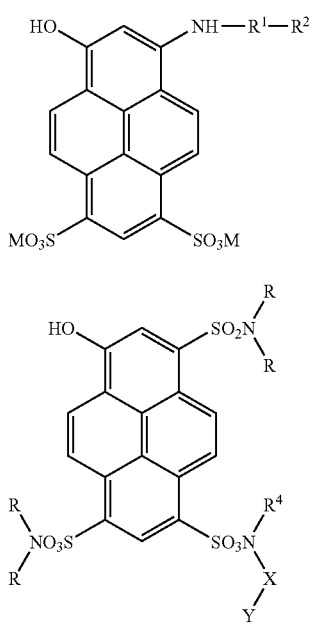

where $R^1$, $R^2$, X and Y represent spacers and conjugating linkers of different compositions, and where R and $R^4$ are hydrogen, alkyl or phenyl substituents. Specific examples are shown in the following tables.

TABLE 1

Spacers and Linkers associated with the compounds of Structure I

| R1 | R2 |
|---|---|
| CO—$(CH_2)$n where n = 1–15 | —COOH, —SH, —$NH_2$, —NCS, —NCO, —$CO_2$—NHS, -Maleimide |
| —CO-PEG | —COOH, —SH, —$NH_2$, —NCS, —NCO, —$CO_2$—NHS, -Maleimide |
| —CO-DEXTRAN | —COOH, —SH, —$NH_2$, —NCS, —NCO, —$CO_2$—NHS, -Maleimide |
| CO$(CH_2)$n-(CONHCHCONH$)_N$<br>\|<br>R | —COOH, —SH, —$NH_2$, —NCS, —NCO, —$CO_2$—NHS, -Maleimide |
| n = 1–15  R = Alkyl, Aryl<br>N = 1–100 | |
| CO-Aryl—$(CH_2)_n$<br>n = 1–15 | —COOH, —SH, —$NH_2$, —NCS, —NCO, —$CO_2$—NHS, -Maleimide |
| CO$(CH_2)_n$—CONH—$(CH_2)_N$—<br>n = 1–15, N = 1–15 | —SH, —$NH_2$, —NCS, —NCO,. -Maleimide, —NHNH2 |
| CO$(CH_2)$n—CONH-PEG<br>n = 1–15 | —SH, —$NH_2$, —NCS, —NCO, -Maleimide, —$NHNH_2$ |
| CO$(CH_2)$n-CONH-DEXTRAN<br>n = 1–15 | —SH, —$NH_2$, —NCS, —NCO, -Maleimide, —$NHNH_2$ |
| $CH_2$—$(CH_2)$n—CONH-X<br>Where X = $(CH_2)$n, n = 1–15<br>= PEG<br>= Dextran | —SH, —$NH_2$, —NCS, —NCO, COONHS, -Maleimide, —$NHNH_2$ |
| $CH_2$—$(CH_2)_n$ | |

TABLE 1-continued

Spacers and Linkers associated with the compounds of Structure I

| R1 | R2 |
|---|---|
| $CH_2$—$(CH_2)$n n = 1–15 | —SH, —$NH_2$, —NCS, -Maleimide, COONHS |

TABLE 2

Spacers and Linkers associated with the compounds of Structure II

| R | R4 | X | Y |
|---|---|---|---|
| $C_nH_{n+2}$,<br>n = 1–10 | $CH_3$,<br>C2H5 | $(CH_2)$N<br>where N = 1–15 | $NH_2$, NCS, SH, COONHS, $NHNH_2$, Maleimide, $NHCOCH_2$I |
| $C_nH_{n+2}$,<br>n = 1–10 | H | Aryl-$(CH_2)_N$—<br>N = 1–15 | $NH_2$, NCS, SH, COONHS, $NHNH_2$, Maleimide, $NHCOCH_2$I |
| $C_nH_{n+2}$,<br>n = 1–10 | H | PEG | COOH, COONHS, Maleimide, SH |
| $C_nH_{n+2}$,<br>n = 1–10 | H | Dextran | COOH, COONHS, Maleimide, SH |
| $C_nH_{n+2}$,<br>n = 1–10 | CH3 | $(CH_2)_n$—<br>CONH—$(CH_2)$m<br>where n,<br>m = 1–15 | $NH_2$, NCS, SH, COONHS, $NHNH_2$, Maleimide, $NHCOCH_2$I |
| $C_nH_{n+2}$,<br>n = 1–10 | C$n$H$n$ + 2, n = 2–10 | $(CH_2)n$—<br>CONH—X where<br>X = PEG,<br>Dextran | $NH_2$, NCS, SH, COONHS, $NHNH_2$, Maleimide, $NHCOCH_2$I |

For a fluorescent label to be most useful in meeting the detection and labeling needs and to replace radioisotopes or colored dyes, it is necessary for the molecule to be highly fluorescent in aqueous solutions. Preferably, the molecule exhibits at least the following characteristics:

1. The molecule should have large quantum yields for excitation and emission. That is, the molecule should absorb and re-emit a substantial fraction of the energy, at least about 60% or higher, of the incident light that is used to excite the molecule.
2. The molecule should exhibit a large Stokes' shift. That is, the molecule should optimally be excited at an excitation wavelength and emitting light at a second emission wavelength that differs from the excitation by at least 60 nm. This will substantially improve signal to noise ratios in detection.
3. The excitation and emission spectra of the fluorogenic substrate should be narrow. This requirement is critical because it enables the fluorescent product to be distinguished from other fluorophores in the same sample. This is useful in reducing background from fluorescence from other sources and for enabling the detection of multiple analytes in the same sample.
4. The molecule should be highly soluble in aqueous media without stacking or other types of solution behavior that evokes photoquenching. It should also be highly fluorescent in aqueous solutions,
5. The fluorescent label should be very photostable. That is, the label should not photobleach or otherwise undergo a loss of molecular brightness during continuous wave excitation and over long periods of time. This is especially important for applications involving multi-photon excitation.

6. The fluorescent label should have a small valued molecular weight, generally less than 100 daltons per monomeric label.
7. The molecule should have a low probability that it will return to the ground state via other mechanisms, e.g., intersystem crossing (phosphorescence) or intramolecular vibrations (IR),
8. For fluorescence polarization applications, the molecule should have an excited state lifetime in the range of 5 to 50 nanoseconds, and,
9. For photon counting applications, the molecule should not have an excited state lifetime of less than 1 nanosecond.

The fluorescent labels of formulae (I) and (II), above, of the present invention meet all of the above noted requirements: They are highly water soluble, and extremely photostable, exhibit large Stokes' shift (see FIG. 1) and narrow excitation and emission bands. In addition, given that it is known that halogenation of fluorophores can reduce their quantum yields by 10-100 fold (compare naphthalene with that of various halonaphthalenes [see Turro, N. J., In: *Modern Molecular Photochemistry*, The Benjamin/Cummings Publishing Co., Inc., 110-111 (1978)], the halogenated fluorescent product of this invention surprisingly and advantageously has an extremely high quantum yield. These features of compounds of structures I through III, in combination, result in the molecules of this invention providing a fluorescent signal that is many orders of magnitude greater than that achievable by such labels as the coumarins, or significantly less subject to photobleaching and photoquenching than fluorescein and its analogs.

Figure 6B:
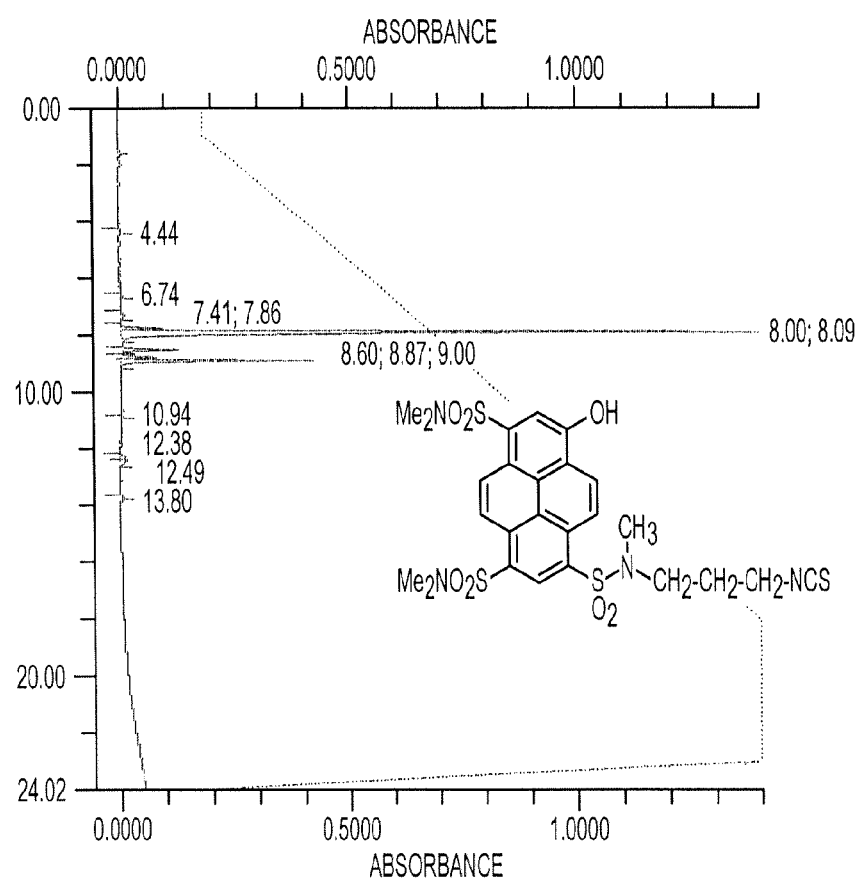
Figure 7:
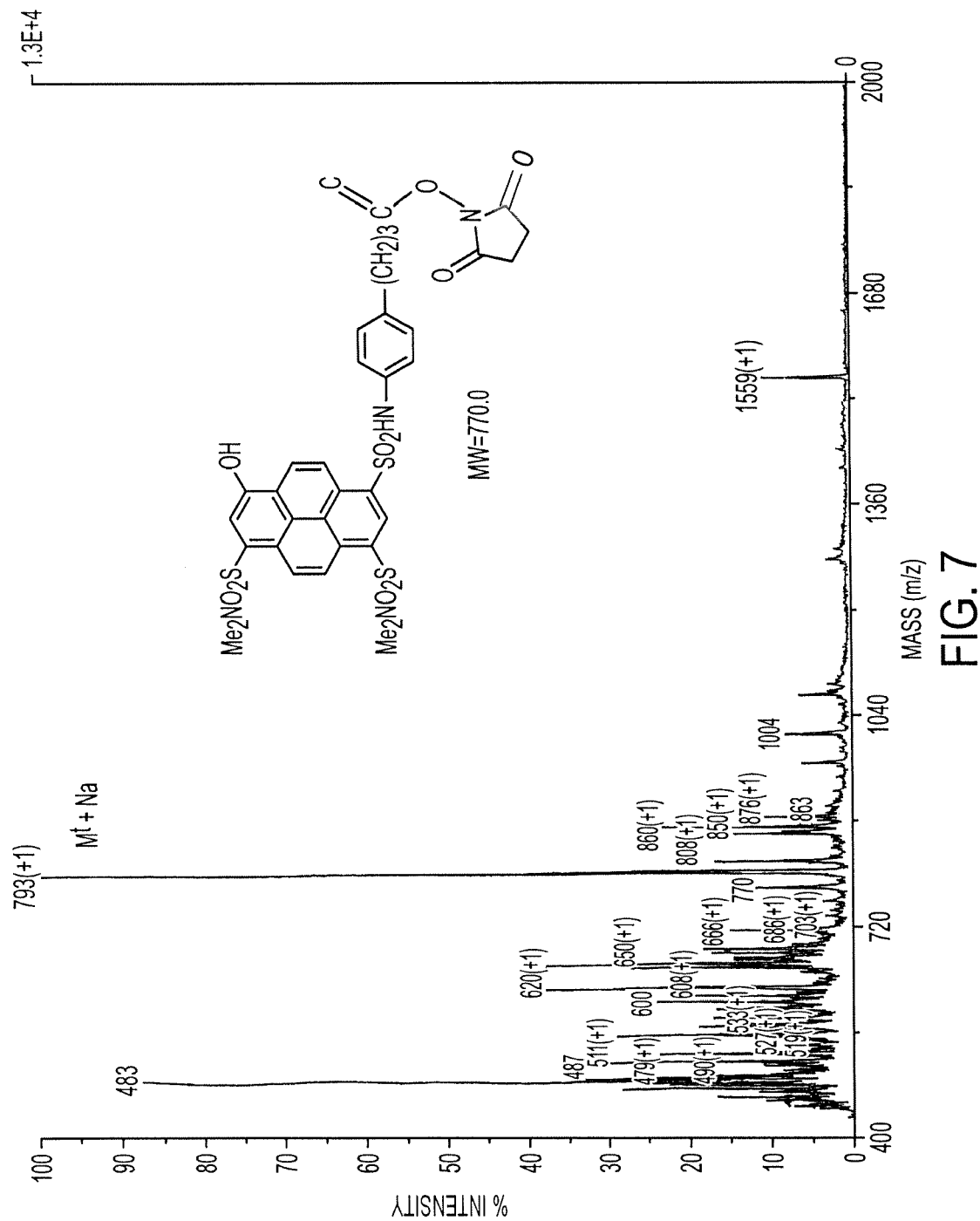
FIG. 7 shows a mass spectrum of the SBO label (compound 17), shown in Scheme 5.
Figure 8:
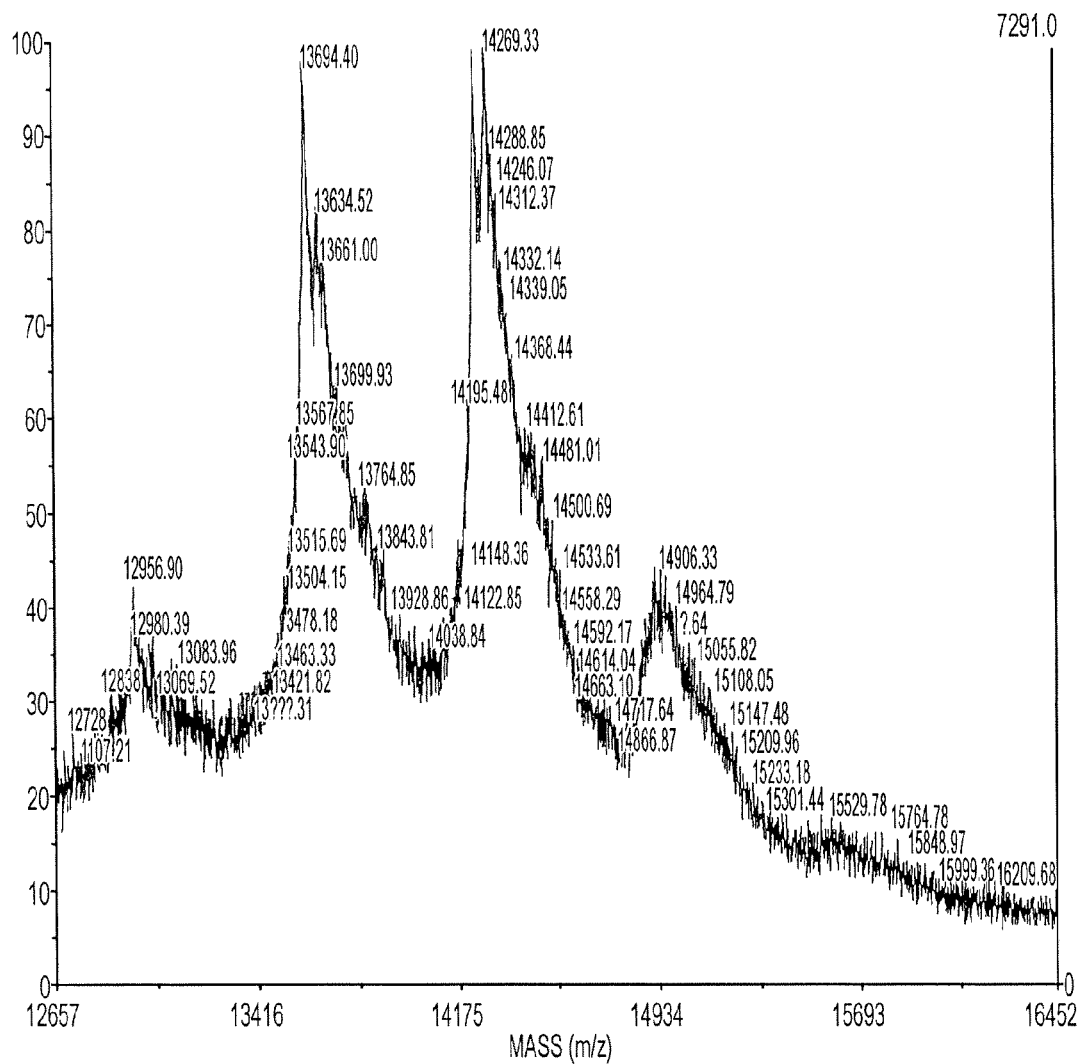
FIG. 8 shows a Maldi Mass Spectrum of a Streptavidin-StarBright Green conjugate as described in Example 1.
Figure 10:
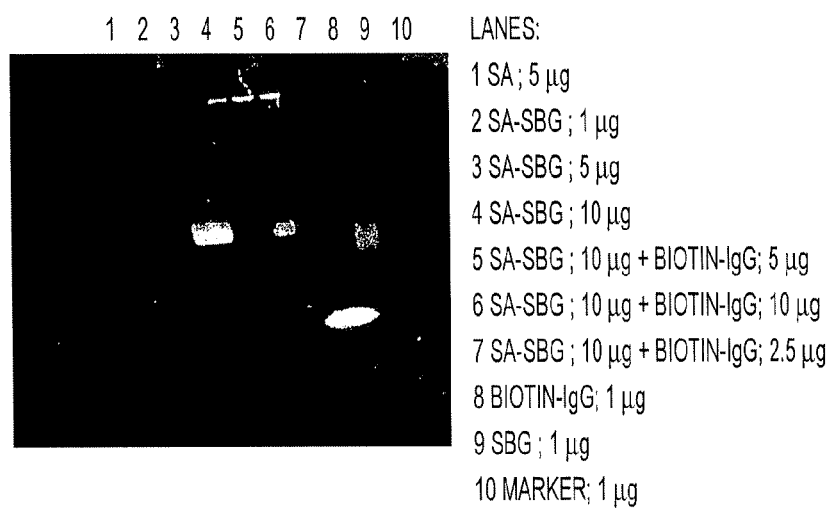
FIG. 10 shows a Gel Shift assay as described in Example 1 of Streptavidin-StarBright Green conjugate reacted with increasing amounts of biotinylated IgG showing an apparent change in molecular weight due to avidin-biotin binding.

In one embodiment of this invention, hydroxyaminopyrene sulphonate is derivatized at the amino group at position 1 on the aromatic ring with spacers that are neither electron donating or withdrawing and which bear a functional group at the ends distal to the aromatic pyrene dye. In one embodiment of this invention, the fluorescent label has an isothiocyano group at the distal end which can react with amino groups on any first binding moiety which is to be used as a probe for a biological target. Such probes can include but are not limited to streptavidin and avidin, monoclonal or polyclonal IgG, oligonucleotides or fusion proteins. Once purified by HPLC as shown in FIG. 8, the label molecule has a mass spectrum as shown in FIG. 10, and a proton NMR as shown in FIG. 6. Similar embodiments are prepared which bear other reactive groups, including but not limited to maleimide, succinimidyl ester, hydrazide, amino, biotinyl, or carboxyl moieties.

Those skilled in the art will recognize that the fluorescent labels of this invention may be linked to any of a number of molecules. Accordingly, nucleic acid probes, nucleosides, antigens, antibodies, proteins, peptides, amino acids, lipids or any other biological or chemical species can be tagged with the labels utilizing chemical linkers and spacers that could readily be carried out by a person skilled in the art having the benefit of the instant disclosure.

Figure 16:
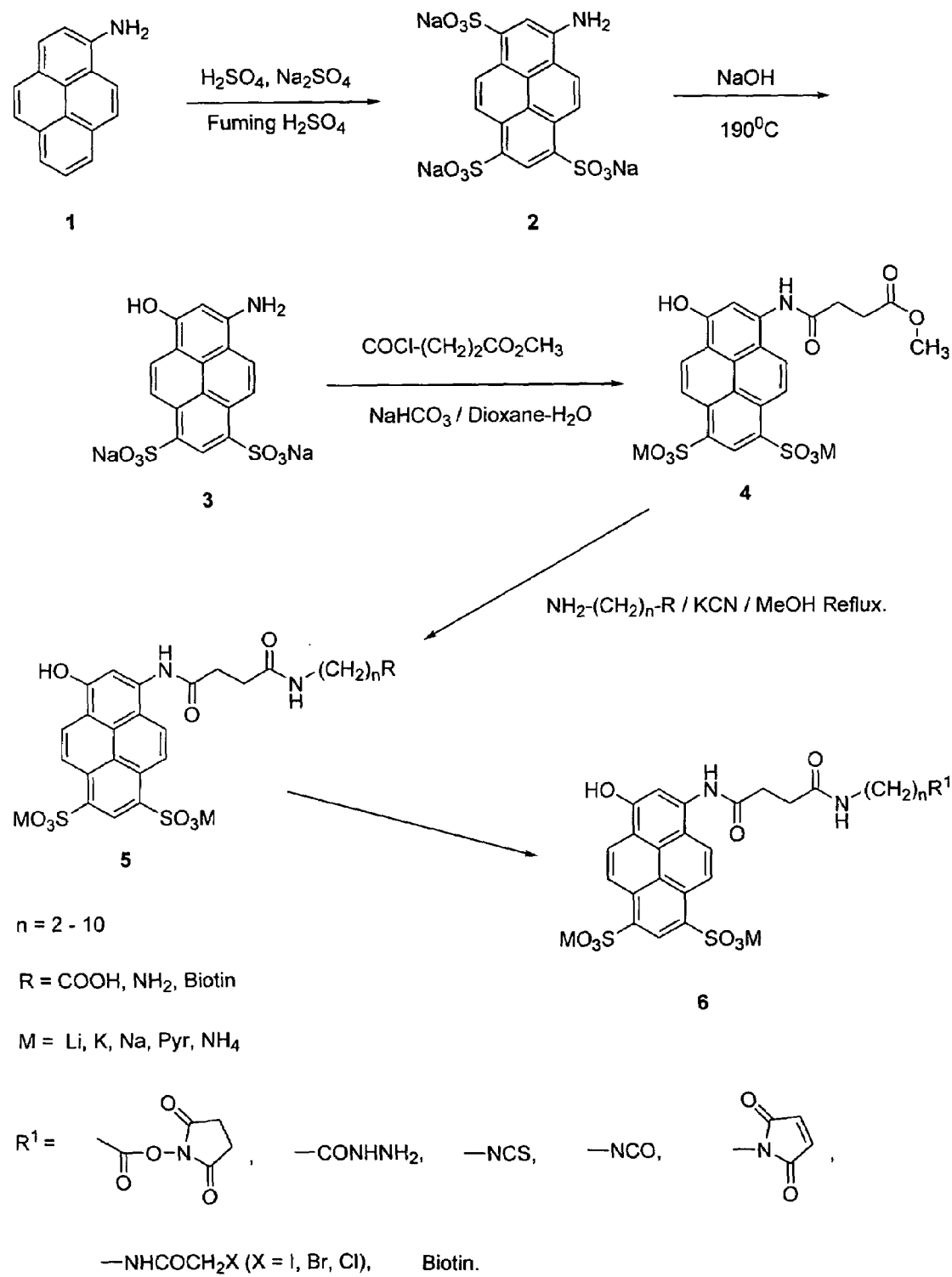
FIG. 16 shows a first synthetic pathway for the synthesis of StarBright Green (SBG) labels.
Figure 17:
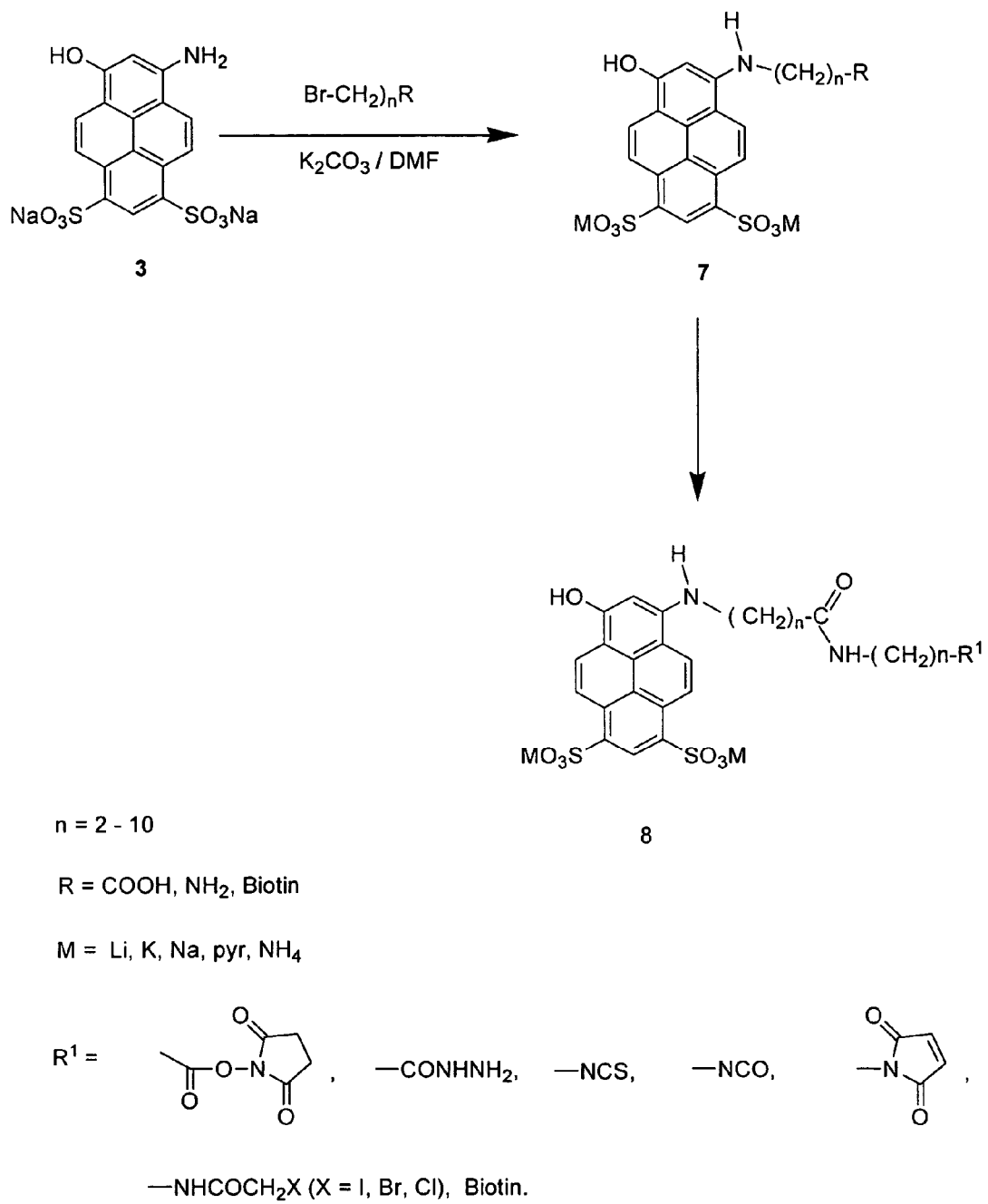
FIG. 17 shows a second synthetic pathway for the synthesis of StarBright Green labels.
Figure 18:
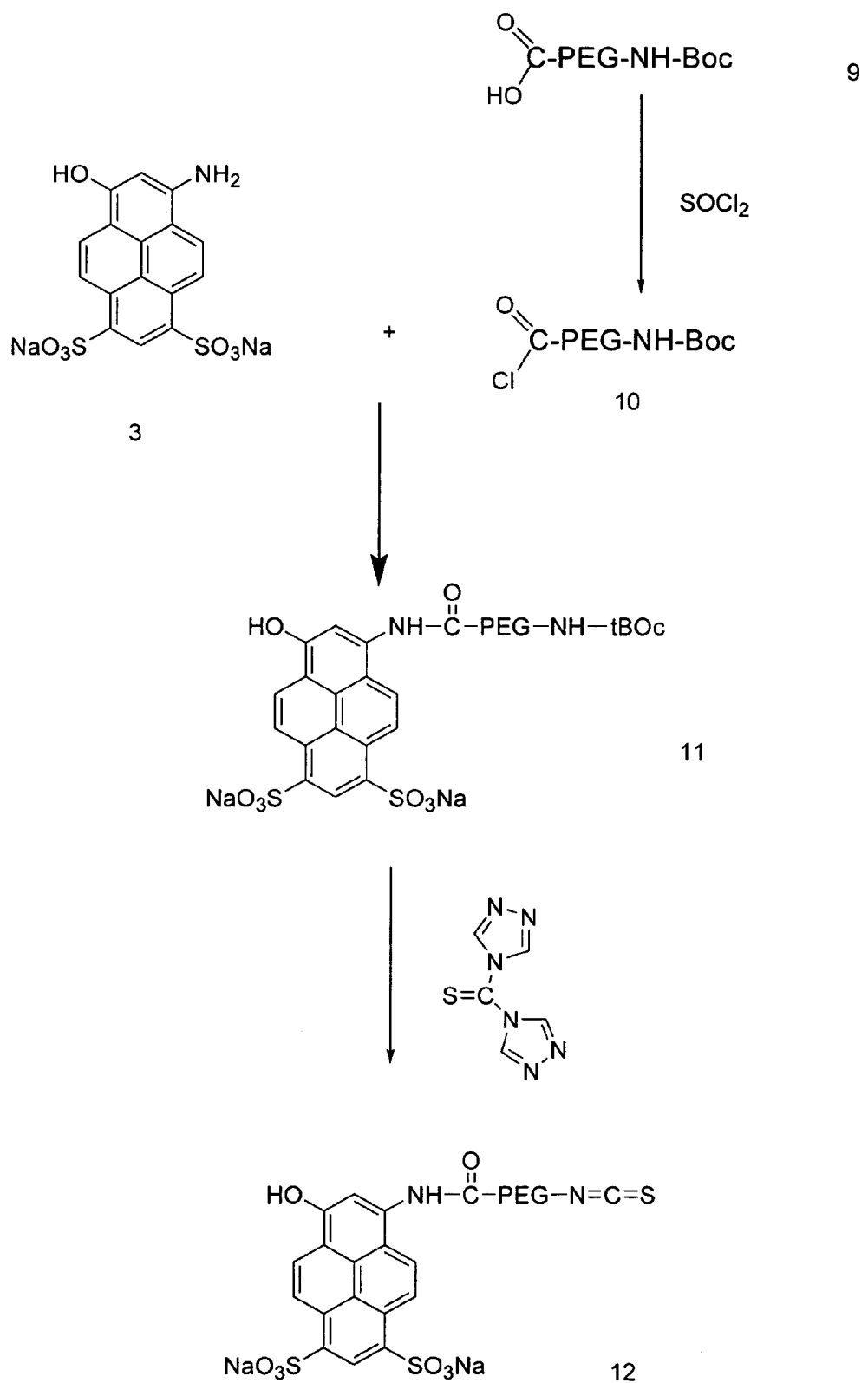
FIG. 18 shows a third synthetic pathway for the synthesis of StarBright Green labels.
Figure 20:
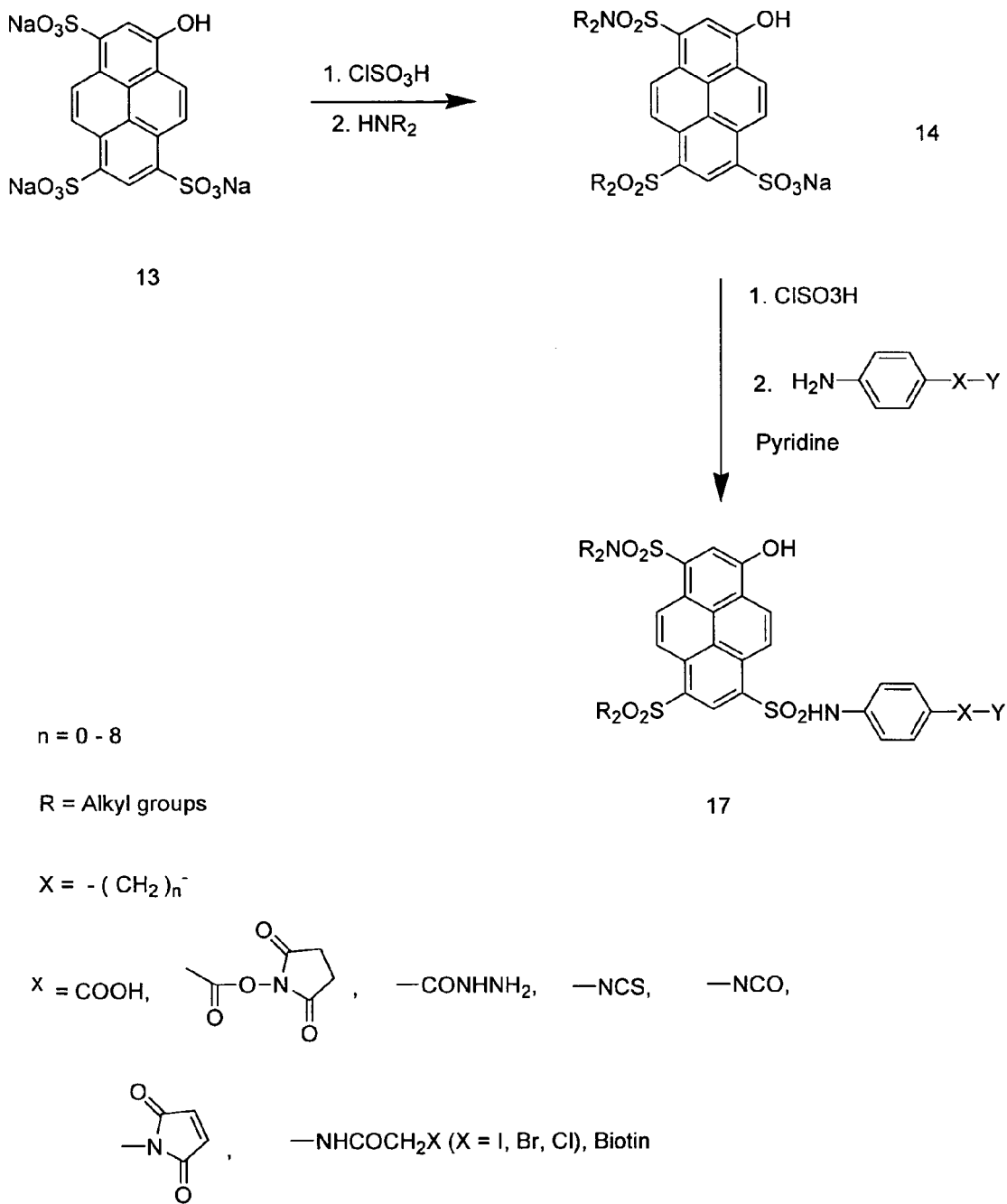
FIG. 20 shows a second synthetic pathway for the synthesis of StarBright Orange labels.
Figure 21:
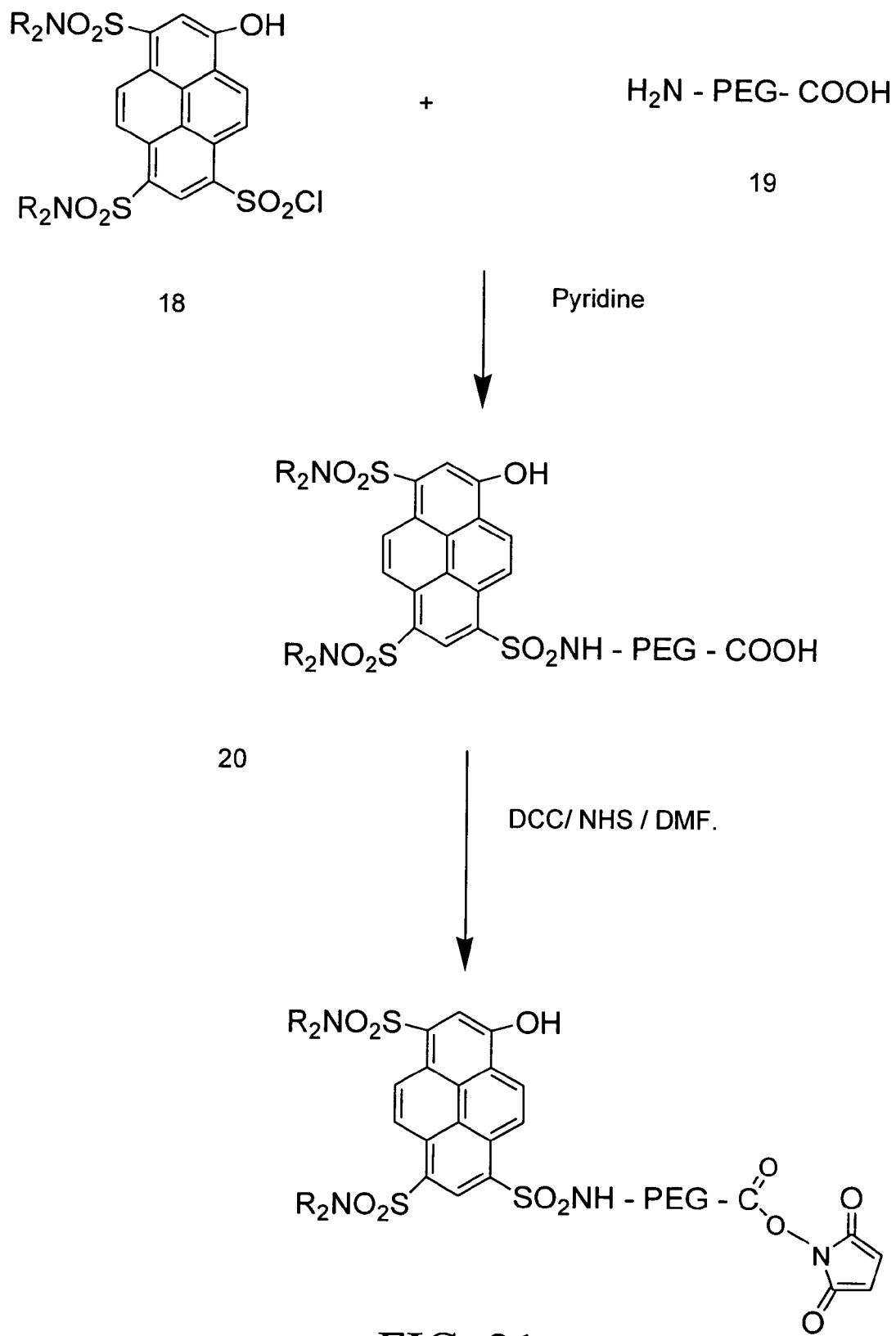
FIG. 21 shows a third synthetic pathway for the synthesis of StarBright Orange labels.

In another embodiment of the subject invention, FIGS. 16-18 show synthetic pathways of the StarBright Green fluorescent labels; and FIGS. 19-21 describe the synthetic pathways of the StarBright Orange fluorescent labels.

In yet another embodiment, the invention provides a reporter system component comprising:

A first reporter subunit (hereinafter a "label") conjugated to a binding moiety including but not limited to such biological probes as: (i) an epitope specific IgG antibody, (ii) a pseudosubstrate peptide for a Protein Kinase C isozyme, (iii) a phospholipid substrate for Phosphatidyl Inositol—5-phosphate kinase (PIP5K), (iv) a sequence specific primer which can hybridize to a complementary oligonucleotide which is to be amplified using PCR, or, (v) a sequence specific detection oligonucleotide probe that can hybridize to a genomic DNA, RNA or mRNA in vitro or in vivo, or, (vi) a low affinity fusion protein that is an inactive subcomponent of an enzyme wherein the binding moiety is capable of a specific association with a second binding moiety such as a cell surface receptor, a kinase enzyme, an oligonucleotide sequence, or a second subcomponent of an enzyme capable of being activated by binding with the binding moiety that is labeled by the reporter subunit.

Yet in another embodiment, the fluorophores of the present invention can be used for signal amplification through (1) incorporation of multiple 5'-triphosphates of nucleosides labeled with StarBight Green or Orange dyes into complementary DNA probes prepared from plasmid DNA through nick translation (J. J. Leary et al., PNAS USA, 80, 4045 (1983)), or by enzymatic addition of series of labeled nucleoside triphosphates at the ends of DNA (L. K. Riley et al., DNA, 5, 333 (1986)), and (2) by attaching multiple of StarBright labels to a polymer which can then be bound to, but not limited to, biomolecules of interest, such as proteins, antibodies, peptides, and nucleic acid molecues In another embodiment, the invention provides a method, assay and/or kit for determining the occurrence of binding between the first and second binding moieties, the method comprising:

a) providing a reporter systems comprising:
   a first component comprising a reporter subunit conjugated to a first binding moiety, and,
   a second component comprising a second binding moiety,
   wherein the first binding moiety is capable of specific association with the second binding moiety to generate a detectable signal, said association being mediated by the binding of the first labeled moiety with the second moiety, as in a heterogeneous fluorescence microscopic detection of a cell surface receptor (the second moiety) by the binding of a StarBright Green labeled IgG that is specific for the cell surface receptor, and,
   detecting the presence or absence of a fluorescence signal.

In a further embodiment, the invention provides a method of screening for binding of the first labeled moiety with members of a plurality of different putative second binding moieties, the method comprising:

a) providing a plurality of reporter systems each comprising:
   a first component comprising a reporter subunit conjugated to a first binding moiety, and,
   one of a plurality of second components, each comprising a second putative binding moiety, wherein, in each of the second components, the plurality of second binding moieties is different;
   wherein the first binding moiety is capable with one of the plurality of putative second binding moieties and is conjugated to a reporter subunit capable of generating a detectable signal if it is bound to one of said different second putative binding moieties;

b) individually combining the first component with each of the plurality of second components to produce a plurality of binding assay samples, each of which includes the first component and a different one of the second components; and, c) detecting the presence or absence of the signal in each of the binding assay samples.

The invention additionally provides proteins (including proteins produced by hybridomas, chemical synthesis or fusion proteins encoded by nucleic acids) or nucleic acids (including chemically synthesized oligonucleotides or nucleic acids produced by transfectants including in vitro transcripts) each of which includes a reporter subunit and a first putative binding moiety. The invention further provides transfected cells transformed by the nucleic acids or viral vectors and hybridomas that will be used to provide proteins and nucleic acids to be labeled as described above.

Materials and Methods

All silica gels chromatography, normal or reverse phase, was performed using silica gel (Merck, grade 1, 230-400 mesh, 60 Å) obtained from Sigma Aldrich. Reagent grade solvents used for synthesis and chromatography were purchased from Aldrich. Reverse phase column chromatography was performed using nanopure water as a solvent.

Fluorescence excitation and emission spectra were measured either using Hitachi F-4500 Fluorescence Spectrophotometer in ratio mode with a rhodamine B quantum counter. For fluorescence polarization experiments, two different detection instruments were used, a BMG Polarstar and an LJL Analyst. Molecular brightness measurements in 96-well and 384-well microtiter plates were performed in the following four instruments: (1) the LJL analyst, (2) the Tecan Ultra, (3) the PerSeptive and, (4) Chromagen's own photon counting instrument as described in U.S. patent application Ser. No. 09/552/803 and its continuation in part.

t-Boc-amino-PEG-carboxylic acid was purchased from Shearwater Polymers. 6-(fluorescein-5-carboxamido)-hexanoic acid succinimidyl ester, single isomer (F-NHS) was purchased from Molecular Probes. Dimethylformamide (DMF), acetonitrile (HPLC Grade), trifluoroacetic acid (TFA), 6-aminohexane, Carbodiimide, sodium phosphate, mono- and dibasic, were all of reagent grades and were purchased from Aldrich. 1-Ethyl-3-(3-dimethylaminopropyl)carbodiimide hydrochloride (EDC), N-hydroxysuccinimidyl sulfonate (sulfo-NHS), and sulfo-NHS-methylacetate (sulfo-NHS-acetate) were purchased from Pierce. Avidin was purchased from Calbiochem. Protein Kinase C alpha was purchased from Panvera, Madison, Wis., and was used following the vendor protocol in 20 mM HEPES, 10 mM MgCl2, 100 uM CaCl2, 100 ug/ml phosphatidylserine (Sigma), 20 ug/ml dioleoylglycerol (Sigma), and 0.03% Triton X-100, pH 7.4. Adenosine-5'-triphosphate (ATP) was from Sigma. EZ-Link Biotin PEO-LC-Amine, catalog #21347, was a product of Pierce. Maldi MS analysis was performed on PerSeptive Biosystem Voyager-DE using alfa-cyno-4-hydroxycinnamic acid (CHCA) as a matrix; the results were sometimes performed using an HP1100 MSD. HPLC purification was performed on BioCad using Vydec C18 column. Fluorescence Polarization (FP) measurements were done on LJL analyst. Fluorescence measurements were performed on Chromagen's own photon counting instrument or using a commercially available Hitachi F-4500 Fluorescence Spectrophotometer. Proton NMR ($^1$H NMR) was performed using a Bruker 500 MHz instrument. Commercial reagents were used without any further purification unless noted. All reactions were followed by thin layer chromatography using EM pre-coated plates of silica gel 60 F254. Silica gels used in flash column chromatography were either EM silica gel 60 (mesh 230-400) for normal phase purification or EM silica gel 60 RP-18 for reversed phase purification.

Following are examples that illustrate procedures for practicing the invention. These examples should not be construed as limiting. All percentages are by weight and all solvent mixture proportions are by volume unless otherwise noted.

I. EXAMPLES RELATING TO PREPARATION OF COMPOUNDS

Example 1

1-Amino-3,6,8-trisulfonyl-pyrene (Compound 2)

Amino-pyrene (434 mg, 2 mmol) was added in small portions to a solution of anhydrous sodium sulfate (1.13 g, 8 mMol) in concentrated sulfuric acid (5 ml). To this mixture was added fuming sulfuric acid (20%, 6 ml) dropwise. The resulting mixture was stirred at 60° C. overnight, then poured into ice and carefully neutralized with 50% sodium hydroxide to pH 7. The solution was concentrated in vacuo to dryness and the solid was extracted with methanol (100 ml) overnight. After evaporating methanol, the crude the product 2 was purified by reversed phase column chromatography to give 0.8 g (77%) of product as a yellow solid. $^1$H NMR (DMSO, 500 MHz): 6.38 (d, 2H), 7.94 (s, 1H), 8.23 (d, 1H), 8.67 (d, 1H), 8.88 (m, 3H); fluorescence (H$_2$O): λ ex=450 nm, λ em=502 nm.

Example 2

1-Amino-3-hydroxy-6,8-disulfonate-pyrene (Compound 3)

Sodium hydroxide (1.6 g, 40 mmol) and H$_2$O (1.8 ml) were heated to 110° C., 2 (1 g, 1.91 mMol) was added to the melt in small portions under stirring. The temperature was raised to 190° C. in 30 min. The solid residue was cooled, acidified with concentrated hydrochloric acid, and the resulting precipitate was filtered off. The solid was extracted with methanol (50 ml). Evaporation of methanol gave 3 as a brown solid, 700 mg. $^1$H NMR (DMSO, 500 MHz): 6.32 (d, 2H), 6.89 (s, 1H), 8.05 (d, 1H), 8.10 (d, 1H), 8.53 (d, 1H), 8.58 (d, 1H), 8.88 (s, 1H); fluorescence (H$_2$O): λ ex=450 nm, λ em=492 nm.

Example 3

3-Hydroxy-6,8-disulfonate-methylsuccinylamino-pyrene (Compound 4)

To a solution of 3 (480 mg, 1.09 mmol) in a mixture of dioxane (15 ml) and H$_2$O (15 ml) was added methyl 4-chloro-4-oxobutyrate (828 mg, 5.50 mMol) at 0° C. The mixture was stirred at 0° C. for 1 h then room temperature overnight. The resulting mixture was extracting with diethyl ether and the aqueous layer was neutralized with sodium bicarbonate to pH 7 and concentrated in vacuo. Purification by reversed phase chromatography afforded the desired product 4 as a yellow solid (150 mg, 25%). $^1$H NMR (DMSO, 500 MHz): 2.72 (t, 2H), 2.88 (t, 2H), 3.65 (s, 3H), 7.96 (d, 1H), 8.20 (d, 1H), 8.30 (d, 1H), 8.89 (d, 1H), 8.95 (d, 1H), 8.97 (s, 1H); fluorescence (H$_2$O): λ ex=450 nm, λ em=492 nm.

Example 4

3-Hydroxy-6,8-disulfonate-(4'-succinyl-6'-amino-hexyl)-pyrene (Compound 5)

A mixture of 4 (150 mg, 0.27 mmol), 1,6-hexanediamine (188 mg, 1.62 mMol) and sodium cyanide (10 mg) in methanol (8 ml) was heated to reflux for 21 h. The solvent was evaporated in vacuo and the residue was purified by reversed phase chromatography to yield 5 as an orange solid (62 mg, 36%). $^1$H NMR (DMSO, 500 MHz): 1.28-1.43 (m, 10H), 2.57 (t, 2H), 2.80-2.82 (m, 2H), 3.0-3.1 (m, 2H), 7.87 (s, 2H), 8.15 (d, 1H), 8.28 (d, 1H), 8.78 (d, 1H), 8.86 (d, 1H), 8.94 (s, 1H), 10.14 (s, 1H); fluorescence ($H_2O$): λ ex=450 nm, λ em=505 nm.

Example 5

3-Hydroxy-6,8-disulfonate-(4'-succinylamino-6'-isothiocyanyl-hexyl)-pyrene (Compound 6)

To a solution of 5 (150 mg, 0.23 mMol) in DMF (20 ml) was added thiocarbonyl diimidazole (84 mg, 0.47 mmol). The mixture was stirred at room temperature for 4 h and precipitated with diethyl ether to give a brown solid. Purification by reversed phase chromatography resulted in the StarBright Green fluorophore 6 as an orange solid (100 mg, 62%). $^1$H NMR (DMSO, 500 MHz): 1.28-1.38 (m, 4H), 1.42 (t, 2H), 1.60 (t, 2H), 2.78 (t, 2H), 3.08 (t, 4H), 3.63 (t, 2H), 7.88-7.93 (m, 1H), 8.05-8.15 (m, 1H), 8.25 (d, 1H), 8.8-8.9 (m, 3H); MS: 632 (M−H), 654 (M−H+Na); fluorescence ($H_2O$): λ ex=450 nm, λ em=503 nm.

Example 6

3-Hydroxy, 6,8-disulfonate-aminoethylacetyl-pyrene (Compound 7)

A mixture of 3 (400 mg, 0.76 mMol), ethyl bromoacetate (206 mg, 1.14 mmol) and potassium carbonate (210 mg, 1.52 mmol) in DMF (4 ml) and DMSO (1 ml) was heated at 70° C. overnight and concentrated in vacuo. Purification by reversed phase chromatography provided 7 as a yellow solid (310 mg, 65%). $^1$H NMR (DMSO, 500 MHz): 1.25 (d, 6H), 4.17 (d, 2H), 5.01 (hept, 1H), 7.22 (t, 1H), 7.68 (s, 1H), 8.33 (d, 1H), 8.74 (d, 1H), 8.90-8.99 (m, 3H); fluorescence (MeOH/$H_2O$): λ ex=450 nm, λ em=502 nm.

Example 7

3-Hydroxy-6,8-disulfonate-aminoacetyl-3'-(6'-aminohexyl)-pyrene (Compound 8)

A mixture of 7 (103 mg, 0.2 mmol), 1,6-diaminohexane (139 mg, 1.2 mmol) and sodium cyanide (8 mg) was heated to reflux for 24 hours. After work-up and Flash Chromatography, as described for compound 5, the desired compound 8 was provided product as a yellow solid (30% yield). The mass spectrum showed a molecular ion at m/e 517. $^1$H NMR (DMSO, 500 MHz) was not clean enough and we used the product for subsequent reactions without further purification.

Example 8

3-Hydroxy-6,8-disulfonate-tBoc-amino-PEG-pyrene (Compound 11)

t-Boc-PEG-COOH (Shearwater Polymers, MW: 3303) 9 (660 mg, 0.2 mmol) was dissolved in 200 ml of thionyl chloride and stirred overnight. The excess of reagent was removed by evaporation under vacuum and the resulting solid thoroughly dried to give compound 10. A sample of it was analyzed by mass spectrometry which gave the desired molecular ion at m/e 3321.5.

The crude acyl chloride 10 (400 mg, 0.12 mmol) was reacted with the hydroxy-amino-pyrene disulfonate 3 (0.1 mmol) in DMF containing diisopropyethylamine (2 mmol.). The mixture was stirred at room temperature overnight. TLC examination of the reaction mixture showed a full consumption of the starting material 3. DMF was then evaporate off under vacuum and the brown residue purified using a reverse phase column leading to compound 11, 200 mg (60%).

Example 9

3-Hydroxy-6,8-disulfonate-1(aminocarbony-1-PEG-Isothiocyano)-pyrene (Compound 3-12)

The compound 11 (100 mg, 0.025 mmol) was first deprotected under mild acidic conditions. The resulting amine was reacted with thiocarbonyl diimidazole (10 mg, 0.05 mmol) in the presence. of diisopropylethylamine (0.1 mmol) in 10 ml of dry DMF. The mixture was stirred at room temperature for 4 hours when TLC showed complete conversion into the isothiocyanate 12. Ether (20 ml) was then added and the precipitate filtered off and dried. Purification using water as a solvent on a reverse phase column allowed the separation of 57 mg (60%) of product 12 as a greenish residue. This product was characterized by HPLC and mass spectrometry.

Example 10

1-Hydroxy-3,6-dimethylsulfonamido-8-sulfonate-pyrene (Compound 14)

1-Hydroxy-trisulfonate-pyrene 13 (1 g, 1.9 mMol) was slowly added at room temperature to chlorosulfonic acid (10 ml). The mixture was then stirred at 60° C. for 6 hours and then carefully poured into ice. The resulting precipitate was filtered off and washed extensively with ice water. The brick red solid obtained was dried under vacuum for 30 minutes and then dissolved in acetone (50 ml). Dimethylamine (15 ml, 2M solution in THF) was added. The resulting solution was stirred for 3 hours and the concenrated under vacuum to give a dark brownish solid. Purification by silica gel column chromatography using $CHCl_3$—MeOH (4:1) provided compound 14 (400 mg, 40%) as a yellow solid which was characterized by NMR and MS. %). $^1$H NMR (DMSO, 500 mHz): 2.79-2.80 (m, 12H), 8.34 (s, 1H), 8.76 (d, 1H), 8.80 (d, 1H), 8.92 (s, 1H), 8.93 (d, 1H), 8.43 (d, 1H); fluorescence (MeOH/$H_2O$): λ ex=490 nm, λ em=545 nm.

Example 11

1-Hydroxy-3,6-di-(dimethylsulfonamido)-8-(3-aminopropyl-methyl-sulfonamido)-pyrene (Compound 15)

To chlorosulfonic acid (8 ml) was added compound 14 (940 mg, 1.83 mMol) at room temperature. The mixture was stirred at room temperature over the weekend and quenched with ice carefully. The solid was filtered off, dried on the vacuum for 30 min. This was added to a solution of N-methyl-3-amino-propane (2M in THF, 20 ml) in acetone (5 ml). The resulting mixture was stirred for 1 h and concentrated in vacuo. Flash chromatography on a silica gel column using $CHCL_3$—MeOH (4:1) provided the desired product 15 as a yellow solid (540 mg, 50%). $^1$H NMR (DMSO, 500 mHz): 1.85-1.90 (m, 2H), 2.65-2.83 (m, 12H), 2.89 (s, 3H), 3.30-3.36 (m,6H), 8.0 (s, 1H), 8.25-8.28 (m, 1H), 8.80-8.90 (m, 3H), 8.97-9.0 (m, 1H); MS (M−H): 581; fluorescence (MeOH/$H_2O$): λ ex=490 nm, λ em=548 nm.

Example 12

1-Hydroxypyrene-3,6-di-(dimethylsulfonamido)-8-(3-isothiocyanato-propyl-methylsulfonamide (Compound 16)

To a solution of 15 (230 mg, 0.40 mMol) in DMF (8 ml) was added thiocarbonyl diimidazole (142 mg, 0.8 mMol). The mixture was stirred at room temperature for a few hours and concentrated in vacuo. Flash chromatography on silica gel column, as described above, provided StarBright Orange, compound 16 as a yellow solid (200 mg, 80%). $^1$H NMR (DMSO, 500 mHz): 1.89 (t, 2H), 2.81-2.84 (m, 12H), 2.86 (s, 3H), 3.27 (t, 2H), 3.66 (t, 2H), 8.33 (s, 1H), 8.85 (d, 1H), 9.0 (s, 1H), 9.05 (d, 1H), 9.14 (d, 1H), 9.20 (d, 1H), 12.0 (s, br, 1H); MS (M−H): 623; fluorescence (MeOH/$H_2O$): λ ex=490 run, λ em=548 nm.

Example 13

1-Hydroxy-3,6-di(dimethylsulfonamido)-8-(4'-succinimidylbutyrate)-phenylsulfonamido-pyrene (Compound 17)

Compound 14 (550 mg, 1.07 mMol) was dissolved in chlorosulfonic acid (10 ml) and stirred at room temperature overnight. The resulting sulfonyl chloride was then precipitated on ice and the solid filtered off and washed with 2×20 ml of cold water. This precipitated was then re-dissolved in 40 ml of dry THF and treated dropwise with a THF (10 ml) solution of 4-aminophenyl Butyric acid (283 mg 2.14 mMol). The resulting dark orange solution was stirred at room temperature overnight when silica gel thin layer chromatography 8:2 methylene-chloride-methanol showed completion. The solvent was then removed by evaporation under vacuum and the product was isolated by silica gel chromatography using 8:2 methylene chloride-Methanol yielding 213.6 mg (32%) of product 17. This product showed a mass of 637.37 expected for this structure.

The above crude butyric acid product (100 mg 0.15 mMol) was dissolved in 5 ml of dry acetonitrile, DCC 36.8 mg (0.178 mMol) was added followed by NHS [20.4] mg, 0.178 mMol. The resulting mixture was stirred at room temperature overnight. TLC Methylene chloride-acetonitrile 7:3 showed completion. The resulting dicyclohexyl urea was filtered off and the filtrate evaporated to dryness. The StarBright Orange dye 17 was then isolated by silica gel chromatography. Yield 86.6 mg. ESI-Mass: calc'd. for $C_{34}H_{34}N_4O_{11}S_3$, 770.0 m/e 793.0 (M+−Na). Fluorescence (DMSO/Phosphate buffer): λ ex=510 nm; λ em=553 nm.

Example 14

3-Hydroxy-6,8-di(dimethylsulfonamido)-8-(succinimidyl-PEG-sulfonamido)-pyrene (Compound 21)

The sulfonyl chloride (compound 18, 53 mg, 0.1 mMol.) was dissolved in 10 ml of a mixture dry THF-Pyridine (1:1). PEG amino acid (400 mg, 0.1 mMol.) in 10 mL DMF was added dropwise over a 10 min. period with stirring. The resulting mixture was stirred overnight at room temperature after which TLC using Methylene Chloride-Methanol (8:2) showed completion. The solvent was evaporated and the residue was purified using silica gel and yielding 250 mg (65%) of pure product 20.

After drying the intermediate 20 (100 mg, 0.026 mMol) was retaken in 10 ml of dry DMF and reacted with DCC (0.052 mmol), followed by 1.2 eq. of N-hydroxysuccinimide. The resulting mixture was then stirred overnight after which completion of the reaction was achieved. Dicyclohexylurea was removed by filtration and the filtrate concentrated and purified by silica gel using 8:2 methylene chloride-Methanol. 62 mg (60%) of pure fluorophore 21 were isolated. Maldi-Mass: m/e 3945, (M+), confirmed the expected structure.

II. EXAMPLES OF APPLICATIONS OF STARBRIGHT GREEN AND STARBRIGHT ORANGE LABELS

Example 15

Conjugation of StarBright Green Isothiocyanate 6 (R1=NCS) to Streptavidin

Streptavidin (10 mg, 167 nMols) was dissolved in 0.1 M sodium borate buffer, pH 9.0 (900 ul) and treated with 70 ul of 100 mM solution of compound 6 in DMF. After adding 30 ul more of DMF, the reaction was gently stirred at 37° C. for 16 hours. The reaction was then diluted to a volume of 4 ml by adding nanopure water and concentrated on centricon-10 spin column at 5000 RP.M until about 100 ul of the retentate was left on the membrane. Added 1.5 ml of 20 mM MOPSO, pH7.0, and again concentrated to a small volume as above. Repeated this procedure 3 times more or until the filtrate shows no fluorescence. The retentate was diluted to 1 ml with 20 mM MOPSO buffer.

Maldi MS analysis of the product showed molecular ions at m/e 13586, 14218 representing loading of 1-2 StarBright dyes per streptavidin molecule (cf., FIG. 8).

BCA protein assay, performed per vendor protocol, showed streptavidin concentration of 0.76 ug/ul (about 85% yield).

Figure 9:
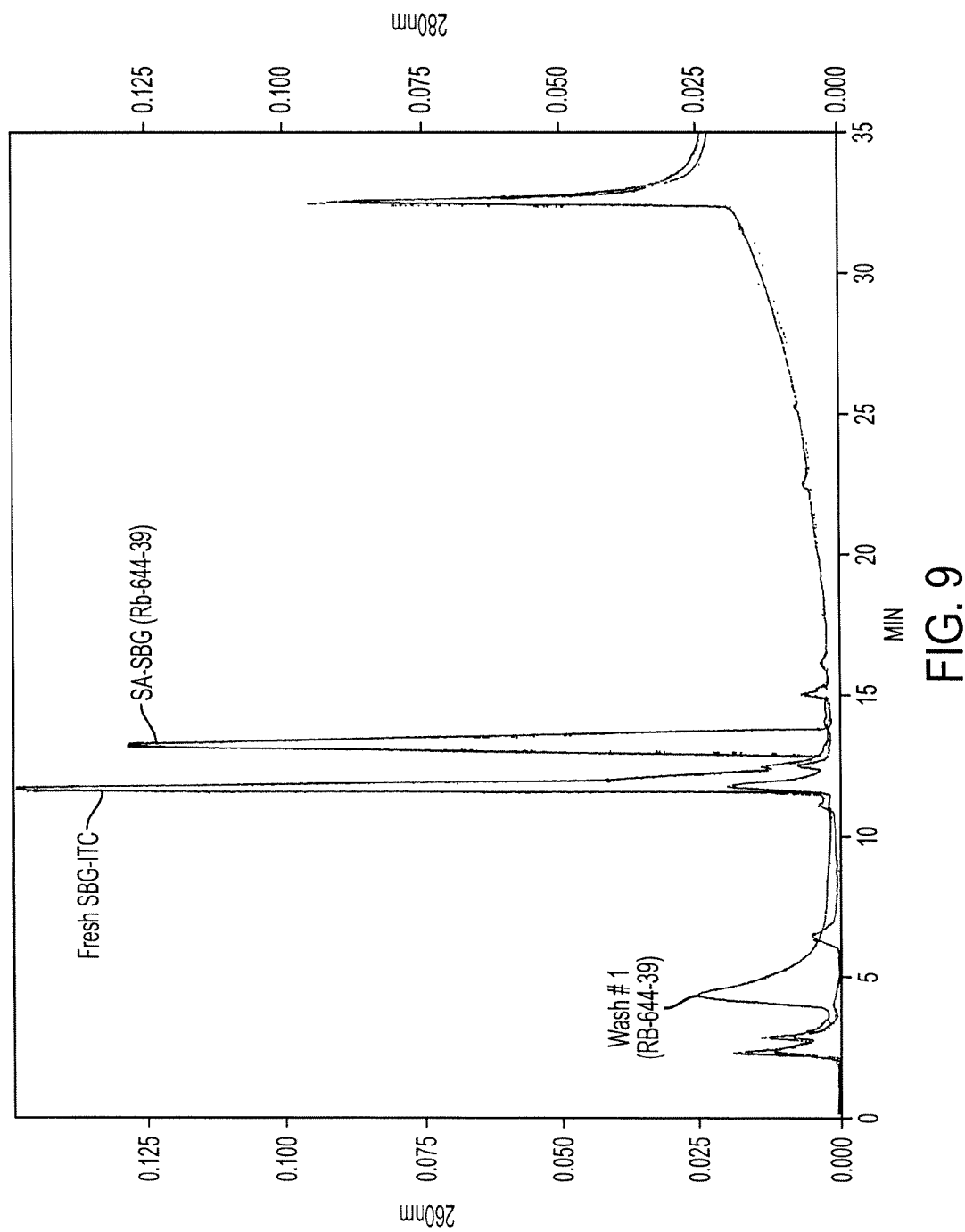
FIG. 9 is an elution profile showing the purification of Streptavidin-StarBright Green conjugate on reversed phase ($C_{18}$) HPLC.

HPLC analysis of the conjugate on a reverse phase $C_{18}$ column using a linear gradient of 0.1% TFA/CH3CN showed virtually no contaminated free streptavidin (cf FIG. 9).

Gel Shift Assay: The integrity of the streptavidin-StarBright Green conjugate (SA-SBG) was further checked by gel shift assay on a 4-20% Tris-Glycine gel. In this experiment, the SA-SBG conjugate was run on the gel along with the conjugate that had been incubated with Biotin-IgG. As shown in the picture of the gel (FIG. 10) under ultraviolet illumination, the lanes 5 through 7 showed a higher MW product fluorescent bands right at top of gel in the well indicating that the formation of a complex IgG-Biotin -SA-SBG. The lanes 2 through 4 which contained only the SA-SBG conjugate showed the fluorescent bands in the middle of the gel.

The gel also showed that there was no contamination of free label with the conjugate.

Example 16

Conjugation of StarBright Green with Goat-x-MS-IgG

The above protocol was applied to the conjugation of StarBright Green with goat-anti-mouse-IgG in essentially the same way as explained above. The unconjugated dye was removed by dialysis on centricon-50 as described above.

Figure 11:
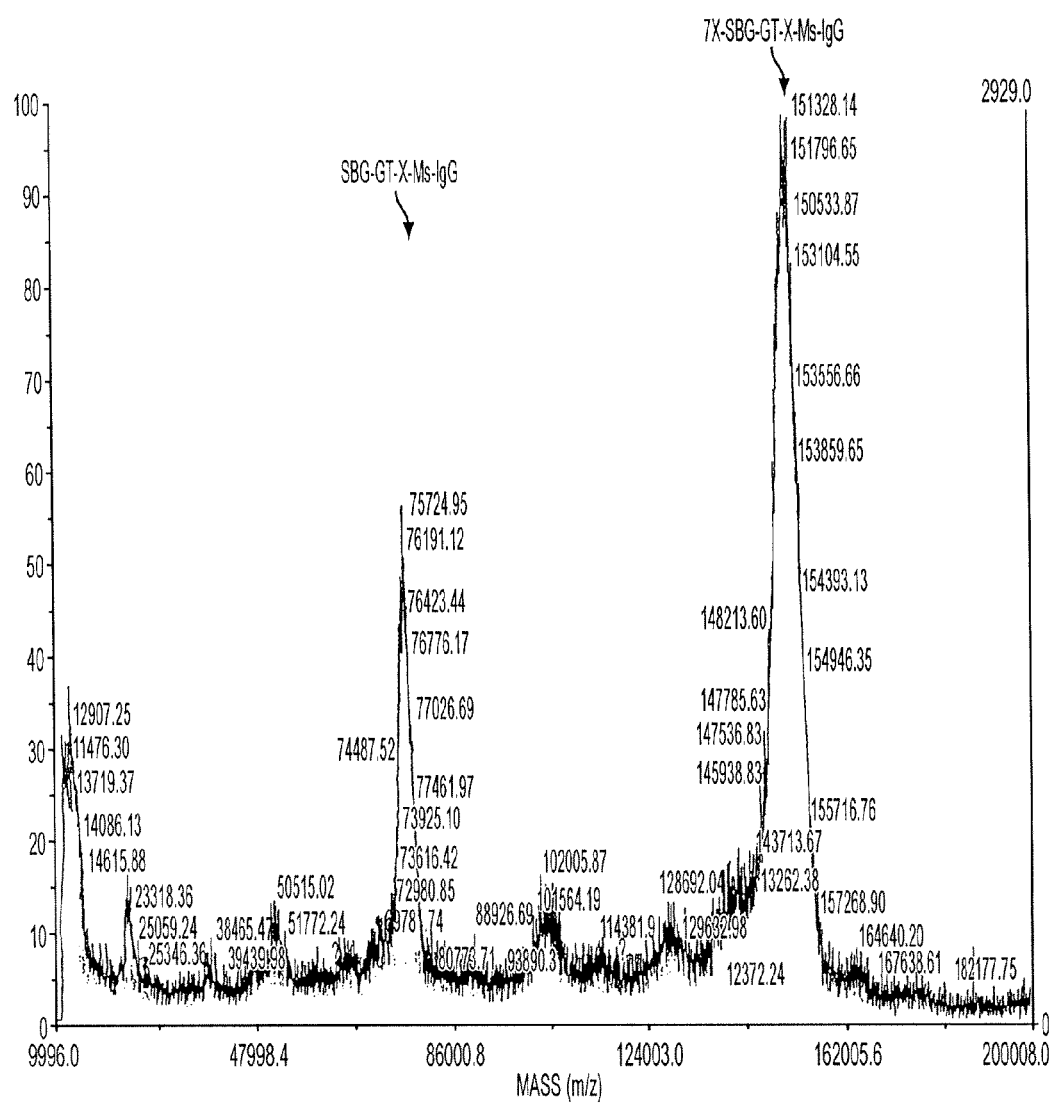
FIG. 11 shows a Maldi-Mass Spectrum of StarBright Green-IgG conjugate as described in Example 1.

The Maldi-Mass Spectrum showed a molecular ion at m/e 151328 (see FIG. 11) which represented the attachment of seven StarBright dye molecules per IgG molecule which has a MW of 146649, per Maldi MS.

Example 17

Conjugation of StarBright Orange Label, 16 ($R_2=R^3=CH_3$, n=3, R NCS), with Streptavidin The protocol of example 1 above when applied to conjugating StarBright Orange label with streptavidin resulted in loading 1-2 dye molecules per unit of streptavidin molecule as shown by Maldi MS, m/e 13582 and m/e 14198 Streptavidin shows a m/e at 12960 in Maldi-MS.

Figure 12:
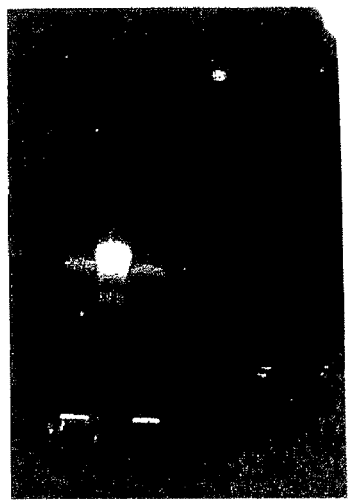
FIG. 12 shows a gel shift assay as described in Example 3 of a Streptavidin-StarBright Orange conjugate reacted with increasing amounts of biotinylated IgG showing an apparent change in molecular weight due to avidin-biotin binding.

Gel Shift assay was also performed as above to confirm that the conjugate obtained was still active as it formed a high MW fluorescent complex with biotin-IgG which stayed at top of gel in the well (FIG. 12).

HPLC analysis was also performed to show that the conjugate was essentially free of any streptavidin.

Example 18

Conjugation of StarBright Orange with Goat-x-MS-IgG

Conjugation was performed performed following the protocol described in example 2. Dialysis was done on Centricon-50 to remove the free label. Maldi MS confirmed the attachment of 6 dyes per IgG molecule.

Example 19

Figure 13:
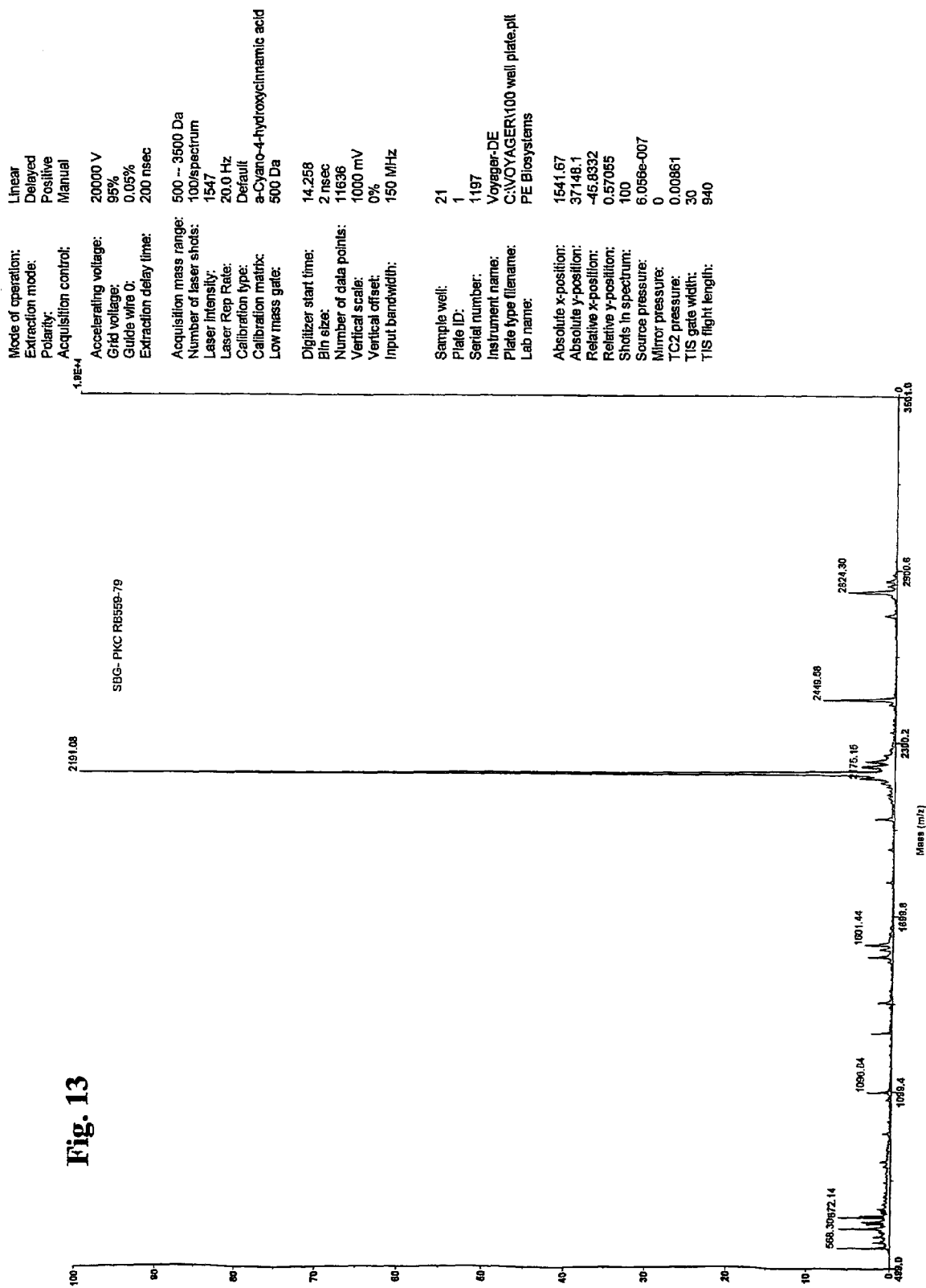
FIG. 13 shows a Maldi Mass Spectrum of a conjugate of StarBright Green with the peptide pseudosubstrate of the isoforms of Protein Kinase C as described in the text.
Figure 14:
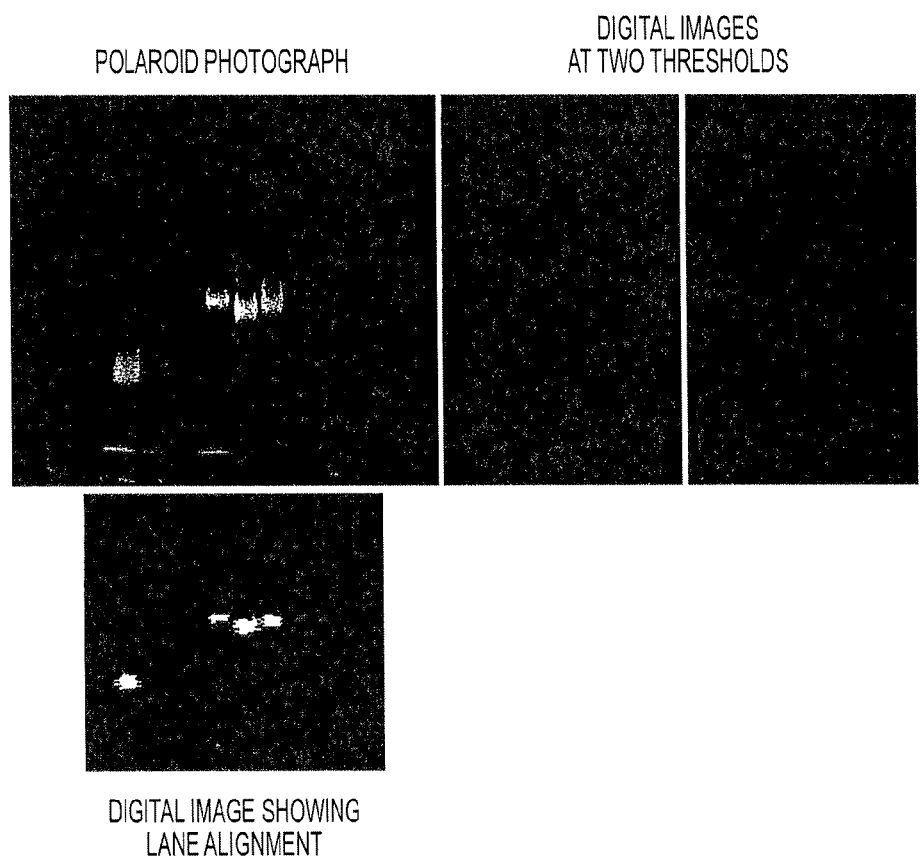
FIG. 14 is a digital image of a polyacrylamide gel showing fluorescent conjugates formed by labeling streptavidin and IgG molecules with the isothiocyanate of StarBright Orange to give labeled reporter moieties having measurable label to probe ratios.

General Protocol of Labeling Peptide Substrates with StarBright Green 6 or StarBright Orange 16 for Assaying Phosphorylases Using Fluorescence Polarization The Protein Kinase C substrate, Arg-Phe-Ala-Arg-Lys-Gly-Ser-Leu-Arg-Gln-Lys-Asn-Val, (2.5 mg, 1603 nMols), was dissolved in 50 mM sodium borate buffer pH9.0 (180 ul), and treated with SBG-NCS, 6 (1.62 mg, 2400 nMols) in 20 ul DMF. The reaction mixture was stirred at room temperature for 16 hours. The Maldi MS analysis of the reaction mixture showed a major ion at m/e 2190 (addition of one SBG molecule) and a minor ion at m/e 1560 due to trace amounts of unreacted starting material. The reaction was then purified by HPLC on a C18 column using a linear gradient of 20% 0.1% TFA/$CH_3CN$ to 100% 0.1% TFA/$CH_3CN$ in 30 minutes at flow rate of 1 ml/min. The fractions collected by monitoring the $OD_{260}$ and $OD_{280}$ nm were analyzed by Maldi MS. The fractions which predominantly gave m/e at 2191 (FIG. 13) were pooled and concentrated under vacuum to dryness at room temperature.

The sequence of the peptide showed that the label was at the terminal amino group. This peptide was used for biological applications which will be the subject of a kinase patent application.

Example 20

Labeling of Oligonucleotides with StarBright Green or Orange Label

The following oligonucleotide sequence, A PCR Primer, was first synthesized on a commonly used Glass Support bearing the nucleoside 'C', using phosphoramidite chemistry on a Expedite DNA Synthesizer:

5'-GCT-GCA-GGT-CGA-GAA-GGC-TTC-AAT-GGA-TTC-3'(SEQ ID NO:1)

While the oligonucleotide was still bound to the glass support, phosphoramidite of the following amino-linker was added at the 5'-end of the oligonucleotide:

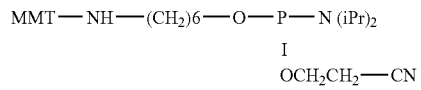

where MMT stands for monomethoxytrityl group.

After the construction of oligonucleotide was complete, the glass support was treated with concentrated ammonium hydroxide solution (2 ml) at 60° C. for 16 hours. After cooling, the ammonium hydroxide solution was separated from the glass beads and concentrated under vacuum to dryness. The residue left was dissolved in 1 ml of 20 mM MOPSO buffer, pH 7.0, filtered through 0.2 uM filter and purified on a C18 column using a linear gradient of 10% acetonitile/0.1M TEAA to 100% acetonitrile in 25 minutes (1 ml/min.). The product peak was collected and concentrated to dryness to obtain the MMT-NH-oligonucleotide

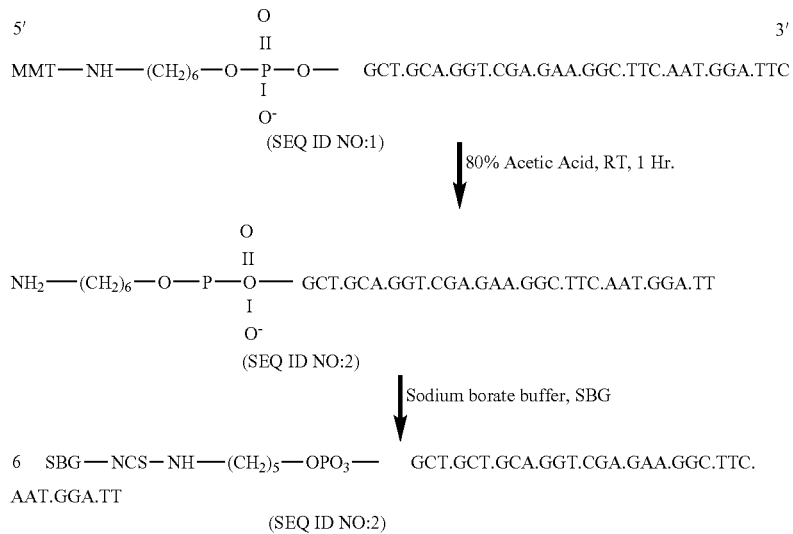

The MMT-NH-olignucleotide was treated with 80% acetic acid in water at RT for 1 hour to remove the MMT group to obtain free amino group at the distal end of the linker attached to the 5'-end of the oligonucleotide. After evaporating the acetic acid off, the oligonucleotide was desalted on Sep-Pak column and then the concentration determined by reading the OD260 nm.

Conjugation of SBG-NCS 6 was accomplished by dissolving 4 OD260 (13.6 nMol) units of oligonucleotide in 50 ul of 0.1M sodium borate buffer, pH 9.0, and treating it with 100 nMols of the StarBright Green 6 (4 ul of 25 mM solution) at 37° C. for several hours.

Figure 15:
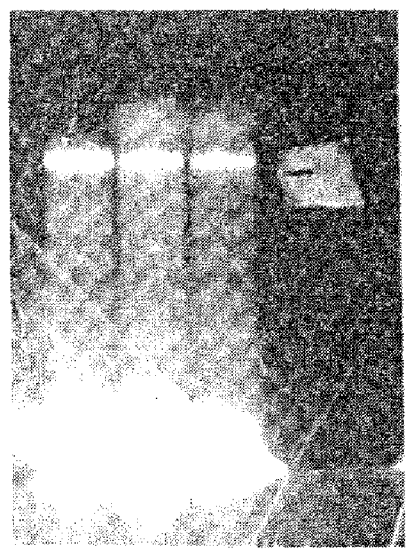
FIG. 15 is a photograph of a polyacrylamide gel showing the fluorescent oligonucleotide labeled with StarBright Green label.

The crude reaction mixture was analyzed by gel electrophoresis on 15% PAGE-7M urea. The fluorescent band (FIG. 15) sliced off the gel, extracted with 100 mM sodium acetate, pH5.5, and then desalted on Sep-pak column to obtain the StarBright Green labeled oligonucleotide.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The complete structure of SBG as attached to an oligonucleotide is shown below:

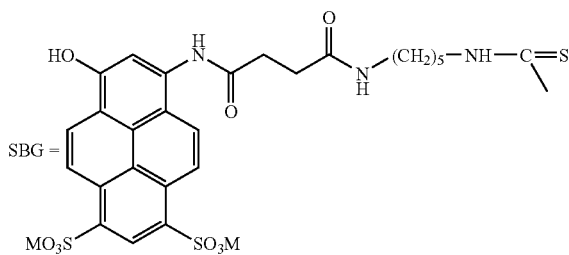

What is claimed is:

1. A fluorescent compound of the general structure:

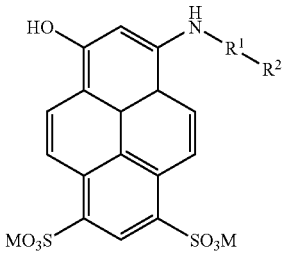

where

M is one of the alkali metals (Li, Na, K), ammonium (NH4), or pyridinium (Py), $R^1$ is a spacer comprised of 2 to 20 carbon, oxygen or nitrogen atoms, with the carbon containing sequences chosen from alkyl, alkenyl, arylalkyl, or alkoxy groups, which can bear any of several substitutions along the carbon chain, including but not limited to amino, carbonyl, carboxyl, hydroxyl, sulfonyl, sulfonamide, oxyethylene, ethylene oxide, or hydroxyl moieties, and, $R^2$=—COOH, —SH, —$NH_2$, —NCS, —NCO, —$CO_2NHS$, $NHNH_2$, -Maleimide, or Hydrazine.

2. The compound, according to claim 1, wherein:
$R^1$=CO—$(CH_2)n$ where n=1-15, and
$R^2$=—COOH, —SH, —$NH_2$, —NCS, —NCO, —$CO_2NHS$, -Maleimide, or Hydrazine.

3. The compound, according to claim 1, wherein:
$R^1$=—CO-PEG, and where
$R^2$=—COOH, —SH, —$NH_2$, —NCS, —NCO, —$CO_2NHS$, -Maleimide or Hydrazide.

4. The compound, according to claim 1, wherein:
$R^1$=—CO— DEXTRAN and where
$R^2$=—COOH, —SH, —$NH_2$, —NCS, —NCO, —$CO_2NHS$, -Maleimide or Hydrazide.

5. The compound, according to claim 1, wherein:

$R^1$=CO$(CH_2)_n$—(CONHCHCONH)$_N$ where R = Alkyl, Aryl, N = 1—100,
         |
         R n=1-15, and
$R^2$=—COOH, —SH, —$NH_2$, —NCS, —NCO, —$CO_2NHS$, -Maleimide, or Hydrazine.

6. The compound, according to claim 1, wherein:
$R^1$=—CO-Aryl-$(CH_2)_n$ where n=1-15 and where
$R^2$=—COOH, —SH, —$NH_2$, —NCS, —NCO, —$CO_2NHS$, -Maleimide, or Hydrazine.

7. The compound, according to claim 1, wherein:
$R^1$=CO$(CH_2)_n$—CONH—$(CH2)_N$—, where n=1-15, and where
$R^2$=—SH, —$NH_2$, —NCS, —NCO, -Maleimide, or —$NHNH_2$.

8. The compound, according to claim 1, wherein:
$R^1$=CO$(CH_2)_n$—CONH—PEG, where n=1-15 and
$R^2$=—SH, —$NH_2$, —NCS, —NCO, -Maleimide, or —$NHNH_2$.

9. The compound, according to claim 1, wherein:
$R^1$=CO$(CH_2)_n$—CONH—DEXTRAN, where n=1-15 and
$R^2$=—SH, —$NH_2$, —NCS, —NCO, -Maleimide, or —$NHNH_2$.

10. The compound, according to claim 1, wherein:
$R^1$=CH2-$(CH_2)_n$—CONH—X, where n=1-15, and where X=$(CH2)_n$, n=1-15
and $R^2$=—SH, —$NH_2$, —NCS, —NCO, -Maleimide, —$CO_2NHS$, or —$NHNH_2$.

11. The compound, according to claim 1, wherein:
$R^1$=CH2-$(CH_2)_n$, where n=1-15 and
$R^2$=—SH, —$NH_2$, —NCS, —NCO, -Maleimide, or —$CO_2NHS$.

12. The compound, according to claim 1, wherein:
$R^1$=$C_nH_{n+2}$, where n=1-15 and
$R^2$=—SH, —$NH_2$, —NCS, —NCO, -Maleimide, or —$CO_2NHS$.

13. A method for detecting biomolecules comprising:
a) providing a fluorescent compound of the general structure

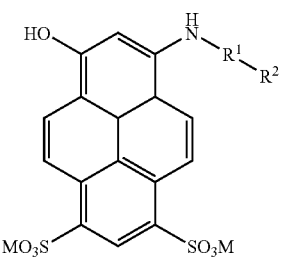

where
M is one of the alkali metals (Li, Na, K), ammonium (NH4), or pyridinium (Py),
$R^1$ is a spacer comprised of 2 to 20 carbon, oxygen or nitrogen atoms, with the carbon containing sequences chosen from alkyl, alkenyl, arylalkyl, or alkoxy groups, which can bear any of several substitutions along the carbon chain, including but not limited to amino, carbonyl, carboxyl, hydroxyl, sulfonyl, sulfonamide, oxyethylene, ethylene oxide, or hydroxyl moieties, and, $R^2$=—COOH, —SH, —$NH_2$, —NCS, —NCO, —$CO_2$—NHS, $NHNH_2$, -Maleimide, or Hydrazine b) detecting the presence or absence of a fluorescence signal.

14. The method, according to claim 13, for use in the labeling of amino or carboxyl groups proteins and peptides.

15. The method, according to claim 13, for use in the labeling of sulfhydryl groups on proteins and peptides.

16. The method, according to claim 13, for use in the labeling of oligonucleotides at the 3' or 5' terminus.

17. The method, according to claim 13, for use in the labeling nucleoside bases in oligonucleotides during chemical synthesis or by random priming.

18. The method, according to claim 13, for use in the labeling nucleoside bases in oligonucleotides during reverse transcription/PCR or PCR.

19. The method, according to claim 13, for use in the labeling of any antigen specific polyclonal or monoclonal IgG.

20. The method, according to claim 13, further comprising the step of conjugating avidin or streptavidin to the fluorescent compound, for use in labeling and detecting any biotinylated compound.

21. The method, according to claim 13, further comprising the step of conjugating any peptide to the fluorescent compound, for use in homogeneous fluorescence polarization assays.

* * * * *

UNITED STATES PATENT AND TRADEMARK OFFICE
CERTIFICATE OF CORRECTION

PATENT NO.       : 7,317,111 B2                                Page 1 of 1
APPLICATION NO.  : 10/669584
DATED            : January 8, 2008
INVENTOR(S)      : Ram Bhatt et al.

It is certified that error appears in the above-identified patent and that said Letters Patent is hereby corrected as shown below:

Column 11,
Line 30,                                should read:
"                                       --

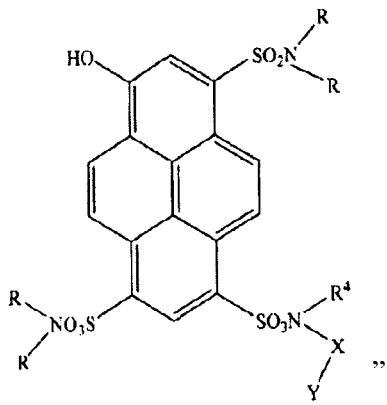 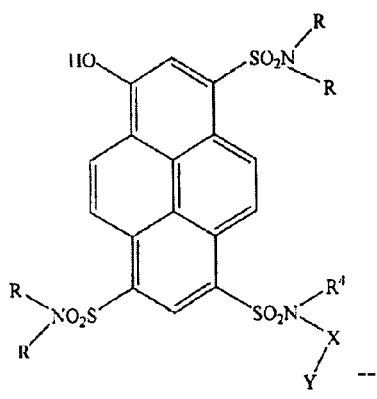

"                                       --

Column 11,
Table 1, Line 58, "-SH, -NH$_2$, -NCS, -NCO,." should read -- -SH, -NH$_2$, -NCS, -NCO,--.

Column 19,
Line 41, "λ ex = 490 run" should read --λ ex = 490 nm--.

Column 23,
Line 23, "GCT.GCT.GCA.GGT.CGA.GAA.GGC.TTC" should read
--GCT.GCA.GGT.CGA.GAA.GGC.TTC--.

Signed and Sealed this

Twenty-seventh Day of May, 2008

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Chemically synthesized PCR primer

<400> SEQUENCE: 1
gctgcaggtc gagaaggctt caatggattc                                   30

<210> SEQ ID NO 2
```

```
<211> LENGTH: 29
<212> TYPE: DNA
<213> ORGANISM: Artificial sequence
<220> FEATURE:
<223> OTHER INFORMATION: Chemically synthesized oligonucleotide obtained
      by treating MMT-NH-oligonucleotide with 80% acetic acid

<400> SEQUENCE: 2
gctgcaggtc gagaaggctt caatggatt                                    29
```